(12) United States Patent
Sims et al.

(10) Patent No.: US 9,687,195 B2
(45) Date of Patent: Jun. 27, 2017

(54) LIFE SIGN DETECTION AND HEALTH STATE ASSESSMENT SYSTEM

(71) Applicants: The General Hospital Corporation, Boston, MA (US); The United States of America, as Represented by the Secretary of the Army, Washington, DC (US)

(72) Inventors: Nathaniel M. Sims, Milton, MA (US); Nhedti Colquitt, Aloha, OR (US); Michael Wollowitz, Chatham, NY (US); Matt Hickcox, Devens, MA (US); Michael Dempsey, Groton, MA (US); Reed J. Hoyt, Framingham, MA (US); Mark J. Buller, Douglas, MA (US); John S. Ames, Wayland, MA (US)

(73) Assignees: THE UNITED STATES OF AMERICA AS REPRESENTED BY THE SECRETARY OF THE ARMY, Washington, DC (US); THE GENERAL HOSPITAL CORPORATION, Boston, MA (US)

( * ) Notice: Subject to any disclaimer, the term of this patent is extended or adjusted under 35 U.S.C. 154(b) by 458 days.

(21) Appl. No.: 14/049,001

(22) Filed: Oct. 8, 2013

(65) Prior Publication Data
US 2014/0249430 A1 Sep. 4, 2014

Related U.S. Application Data

(63) Continuation of application No. 13/744,865, filed on Jan. 18, 2013, now abandoned, which is a
(Continued)

(51) Int. Cl.
*A61B 5/00* (2006.01)
*G06F 19/00* (2011.01)
(Continued)

(52) U.S. Cl.
CPC ........ *A61B 5/6804* (2013.01); *A61B 5/02055* (2013.01); *A61B 5/113* (2013.01);
(Continued)

(58) Field of Classification Search
CPC .. G06F 19/34; G06F 19/3431; G06F 19/3418; G06F 19/345; G06F 19/3487;
(Continued)

(56) References Cited

U.S. PATENT DOCUMENTS

| 5,235,989 A | 8/1993 | Zomer |
| 5,928,157 A | 7/1999 | O'Dwyer |

(Continued)

FOREIGN PATENT DOCUMENTS

EP 0 488 438 A2 9/1991

*Primary Examiner* — William Thompson
*Assistant Examiner* — Marie Archer
(74) *Attorney, Agent, or Firm* — Drinker Biddle & Reath LLP

(57) ABSTRACT

A wearable platform embodied in a belt or patch provides physiological monitoring of soldiers during field operations or trauma victims at accident sites and makes health state assessments. The platform includes sensors for heart rate, body motion, respiration rate and intensity, and temperature and further contains a microprocessor and short range transmitter. An analog circuit running an algorithm obtains the R-wave period from the EKG signal and produces electrical pulses with the period between pulses corresponding to the R-wave period. A rule based processing engine having an evaluation algorithm is capable of making a medical evaluation of subject condition and determines a confidence level for the evaluation. The rules are subject to variation depend-
(Continued)

ing upon the subject population. The information is communicated wirelessly to a local hub for relay to a remote monitor.

16 Claims, 34 Drawing Sheets

Related U.S. Application Data continuation of application No. 10/595,672, filed as application No. PCT/US2004/036587 on Nov. 3, 2004, now abandoned.

(60) Provisional application No. 60/517,149, filed on Nov. 4, 2003.

(51) Int. Cl.
*A61B 5/113* (2006.01)
*A61B 5/0205* (2006.01)

(52) U.S. Cl.
CPC .......... *A61B 5/1135* (2013.01); *A61B 5/6831* (2013.01); *A61B 5/72* (2013.01); *G06F 19/34* (2013.01); *G06F 19/345* (2013.01); *G06F 19/3418* (2013.01); *G06F 19/3431* (2013.01); *G06F 19/3487* (2013.01); *G06F 19/3493* (2013.01); *A61B 2562/0261* (2013.01)

(58) Field of Classification Search
CPC ..... G06F 19/3493; A61B 5/0002; A61B 5/02; A61B 5/11; A61B 5/68–5/6807
See application file for complete search history.

(56) References Cited

U.S. PATENT DOCUMENTS

| | | | |
|---|---|---|---|
| 6,160,478 A | 12/2000 | Jacobsen et al. | |
| 6,198,394 B1 | 3/2001 | Jacobsen et al. | |
| 6,385,473 B1 | 5/2002 | Haines et al. | |
| 6,454,708 B1* | 9/2002 | Ferguson ........... | A61B 5/02055 128/903 |
| 6,461,307 B1 | 10/2002 | Kristbjarnarson et al. | |
| 6,470,893 B1* | 10/2002 | Boesen ................ | A61B 5/002 128/899 |
| 7,054,784 B2 | 5/2006 | Flentov et al. | |
| 7,256,708 B2 | 8/2007 | Rosenfeld et al. | |
| 7,740,588 B1* | 6/2010 | Sciarra ................ | A61B 5/0205 600/483 |
| 2002/0081558 A1* | 6/2002 | Finitzo ............... | A61B 5/04845 434/262 |
| 2002/0169584 A1* | 11/2002 | Fu ........................ | A61B 5/0022 702/188 |
| 2004/0073460 A1* | 4/2004 | Erwin ................... | G06F 19/325 705/2 |
| 2004/0122295 A1* | 6/2004 | Hatlestad ............ | A61B 5/0031 600/300 |
| 2004/0242972 A1 | 12/2004 | Adak et al. | |
| 2005/0054941 A1* | 3/2005 | Ting ..................... | A61B 5/0408 600/529 |
| 2005/0177393 A1 | 8/2005 | Sacco et al. | |

* cited by examiner

FIG. 9
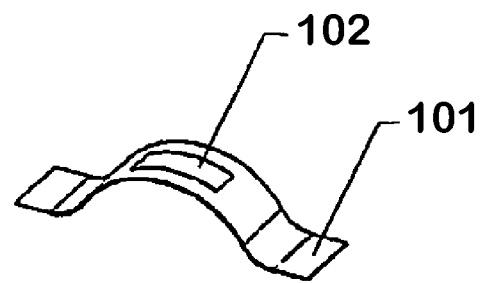
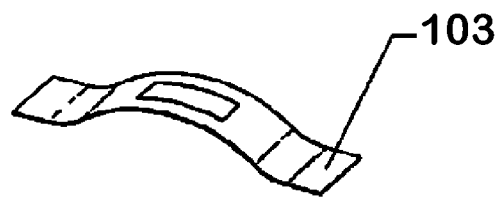
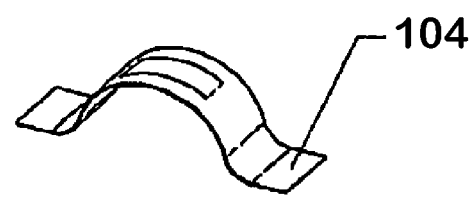
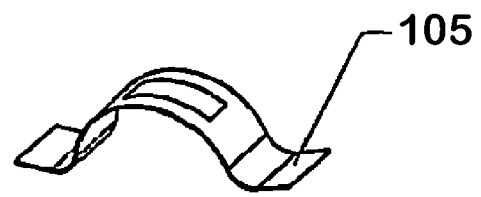
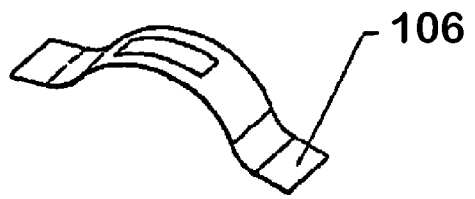

FIG. 10
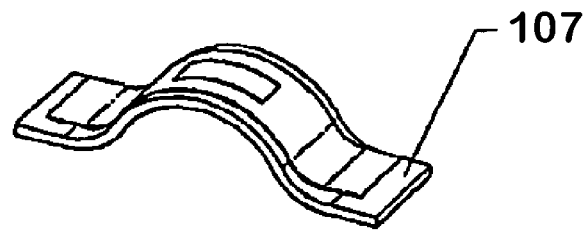
107
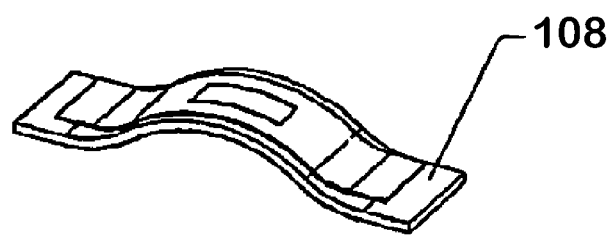
108
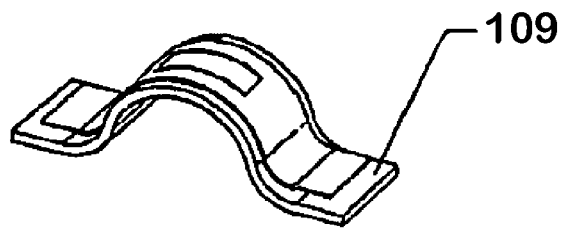
109
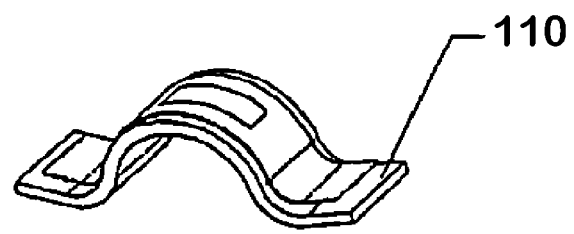
110
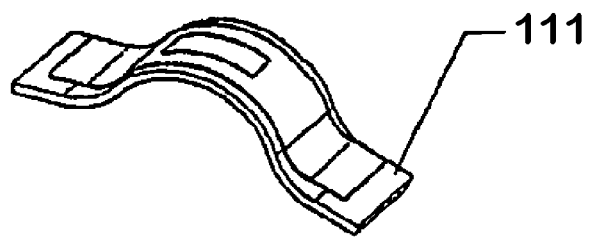
111

FIG. 34

Table 1. LSDS Platform Parameters and Error Conditions

| Sensor | Primary Life Sign Parameter | Additional Data | Error Conditions from Sensor |
|---|---|---|---|
| R-Wave Detector | HR | Presence of signal (Yes or No) <br> Heart rate variability | Leads Off <br> Noisy Lead <br> Signal not detected <br> Out of range – high <br> Out of range – low <br> Sensor INOP |
| Temperature Sensor | Temp (an estimate of core body temperature value based on External Body Temperature as affected by ambient temperature) | External body temperature | Signal not detected <br> Out of range – high <br> Out of range – low <br> Sensor INOP |
| Accelerometer | Speed of motion (None, Slow, Medium, High, or Off-scale Shock) | Body Position (Vertical/Upright, Vertical/Upside-down, Horizontal) | Sensor INOP |
| Respiration | Presence of Respiration (Yes or No) | Respiration Rate <br> Tidal volume indicator <br> Time since last breath <br> Presence of motion | Bad signal (voltage too high or too low) <br> No breath detected <br> Out of range – high <br> Out of range – low <br> Sensor INOP |
| Other Information from Sensor Platform | Platform ID (device serial number, or possibly soldier ID number) | Time Stamp of data packet | Low Battery |

FIG. 35

Table 2. Default Health State Classification Descriptions

| Overall Health State | Color Code |
|---|---|
| Alive | ♡ Green |
| Alive, but significantly outside "normal" | ♡ Yellow |
| Dead | ♥ Red |
| Uncertain (Incomplete or conflicting information from sensors) | ♡ Blue |
| SENSOR PLATFORM NOT OPERATING (Determined by receiving platform, e.g., no data received at for a given prolonged interval) | ♥ Black |

FIG. 36A

Table 3. Default Life Signs Interpretation Rules for Alive/Green and Dead/Red States

| Available Parameters | Interpretation Rule | |
|---|---|---|
| | Alive/Green | Dead/Red |
| HR only | HR ≤ 160 BPM and HR ≥ 40 BPM for 8 seconds or more | HR = 0 for 4 minutes or more<br><br>HR <30 BPM for 10 minutes or more |
| RR only | RR ≤30 breaths/minute and RR ≥ 8 breaths/minutes for 8 seconds or more | RR = 0 for 5minutes or more |
| Acceleration/Position only | Insufficient to determine this state | Insufficient to determine this state |
| Temp only | Insufficient to determine this state | Insufficient to determine this state |
| HR and RR | [HR ≤ 160 BPM and HR ≥ 40 BPM and (RR ≤30 breaths/minute and ≥ 8 breaths/minutes)] for 8 seconds or more | HR = 0 and RR = 0 for 4 minutes or more |
| HR and Acceleration/Position | (HR ≤ 160 BPM and HR ≥ 40 BPM) and any acceleration value and any position value for 8 seconds or more<br><br>(HR > 160 /BPM and HR ≤ 220 BPM) and (Acceleration is Medium or Fast for any Position value) for 8 seconds or more | HR = 0 and Acceleration is NONE (for any position value) for 4 minutes or more |
| HR and Temp | (HR ≤ 160 BPM and HR ≥ 40 BPM) and (Temp = NORMAL) for 8 seconds or more | HR = 0 and Temp ≠ NORMAL for 4 minutes or more |
| RR and Acceleration /Position | RR ≤30 breaths/minute and RR ≥ 8 breaths/minutes and any acceleration value and any position value for 8 seconds or more<br><br>[(RR >30 breaths per minute and RR ≤ 45 breaths per minute) and Acceleration is Fast, for any Position value)] for 8 seconds or more | RR = 0 and Acceleration = NONE (any Position value) for 5 minutes or more |
| RR and Temp | RR ≤30 breaths/minute and RR ≥ 8 breaths/minutes and Temp is NORMAL for 8 seconds or more | RR = 0 and Temp ≠ NORMAL for 5 minutes or more |
| Acceleration /Position and Temp | Insufficient to determine this state | Insufficient to determine this state |
| HR, RR, and Acceleration /Position | [(HR ≤ 160 BPM and HR ≥ 40 BPM) and (RR ≤30 breaths/minute and RR ≥ 8 breaths/minutes) and (any acceleration value and any position value)] for 8 seconds or more<br><br>[(HR > 160 /BPM and HR ≤ 220 BPM) and (RR >30 breaths per minute and RR ≤ 45 breaths per minute) and Acceleration is Fast, for any Position value)] for 8 seconds or more | [(HR = 0) and (RR = 0) and (Acceleration is NONE for any Position value)] for 4 minutes or more |
| HR, RR, and Temp | [(HR ≤ 160 BPM and HR ≥ 40 | [(HR = 0) and (RR = 0) and (any |

FIG. 36B

|  | BPM) and (RR ≤30 breaths/minute and RR ≥ 8 breaths/minutes) and (Temp is NORMAL)] for 8 seconds or more | Temp ≠ NORMAL)] for 4 minutes or more |
|---|---|---|
| HR, Acceleration/Position and Temp | [(HR ≤ 160 BPM and HR ≥ 40 BPM) and (any acceleration value and any position value) and Temp is NORMAL]for 8 seconds or more<br><br>[(HR > 160 /BPM and HR ≤ 220 BPM) and (RR >30 breaths per minute and RR ≤ 45 breaths per minute) and (Acceleration is Fast, for any Position value) and Temp is NORMAL] for 8 seconds or more | [(HR = 0) and (Acceleration is NONE for any position value) and Temp ≠ NORMAL )] for 4 minutes or more |
| RR, Acceleration /Position and Temp | [(RR ≤30 breaths/minute and RR ≥ 8 breaths/minutes) and (any acceleration value and any position value) and Temp is NORMAL] for 8 seconds or more<br><br>[(RR >30 breaths per minute and RR ≤ 45 breaths per minute) and (Acceleration is Fast, for any Position value) and Temp is NORMAL] for 8 seconds or more | [(RR = 0) and (Acceleration = NONE for any Position value) and Temp ≠ NORMAL)] for 5 minutes or more |
| HR, RR, Acceleration /Position and Temp | [(HR ≤ 160 BPM and HR ≥ 40 BPM) and (RR ≤30 breaths/minute and RR ≥ 8 breaths/minutes) and (any acceleration value and any position value) and Temp is NORMAL] for 8 seconds or more<br><br>[(HR > 160 /BPM and HR ≤ 220 BPM) and (RR >30 breaths per minute and RR ≤ 45 breaths per minute) and Acceleration is Fast, for any Position value) and Temp is NORMAL] for 8 seconds or more | [(HR = 0) and (RR = 0) and (Acceleration is NONE for any Position value) and Temp ≠ NORMAL] for 4 minutes or more |

FIG. 37

Table 4. Default Life Signs Interpretation Rules for Alive/Yellow State

| Available Parameters | Interpretation Rules |
|---|---|
| HR only | [(HR < 40 BPM and HR ≠ 0 BPM) or (HR> 160 BPM)] for 8 seconds or more |
| RR only | [(RR<8 breaths/min and RR ≠ 0 breaths/min) or RR > 30 breaths/min)] for 8 seconds or more |
| Acceleration only | Insufficient to determine this state |
| Temp only | Insufficient to determine this state |
| HR and RR | [(HR < 40 BPM and HR ≠ 0 BPM) and/or (HR> 160 BPM) or (RR<8 breaths/min and RR ≠ 0 breaths/min) or RR > 30 breaths/min)] for 8 seconds or more |
| HR and Acceleration | [(HR < 40 BPM and HR ≠ 0 BPM and any acceleration value) or (HR> 160 BPM and Acceleration is NONE)] for 8 seconds or more |
| HR and Temp | [(HR < 40 BPM and HR ≠ 0 BPM for any Temp value) or (HR> 160 BPM and Acceleration < Medium for any Position value and any Temp value)] for 8 seconds or more |
| RR and Acceleration /Position | [(RR<8 breaths/min and RR ≠ 0 breaths/min and any acceleration value and any position value) or (RR > 30 breaths/min and Acceleration < Medium for any Position value)] for 8 seconds or more |
| RR and Temp | [(RR<8 breaths/min and RR ≠ 0 breaths/min and any Temp value) or (RR > 30 breaths/min and any Temp value)] for 8 seconds or more |
| Acceleration /Position and Temp | Insufficient to determine this state |
| HR, RR, and Acceleration /Position | [(HR < 40 BPM and HR ≠ 0 BPM) and/or (RR<8 breaths/min and RR ≠ 0 breaths/min) for any Acceleration value and any Position value] for 8 seconds or more<br><br>[(HR> 160 BPM and/or RR > 30 breaths/min) and Acceleration < Medium for any position value] for 8 seconds or more |
| HR, RR, and Temp | [(HR < 40 BPM and HR ≠ 0 BPM) and/or (RR<8 breaths/min and RR ≠ 0 breaths/min) and any Temp value] for 8 seconds or more<br><br>[(HR> 160 BPM and/or RR > 30 breaths/min) and any Temp value] for 8 seconds or more |
| HR, Acceleration/Position and Temp | [(HR < 40 BPM and HR ≠ 0 BPM and any acceleration value and any Temp value) or (HR> 160 BPM and Acceleration < Medium and any Temp value)] for 8 seconds or more |
| RR, Acceleration /Position and Temp | [(RR<8 breaths/min and RR ≠ 0 breaths/min and any acceleration value and any position value and any Temp value) or (RR > 30 breaths/min and Acceleration < Medium for any position value and any Temp value)] for 8 seconds or more |
| HR, RR, Acceleration /Position and Temp | [(HR < 40 BPM and HR ≠ 0 BPM) and/or (RR<8 breaths/min and RR ≠ 0 breaths/min) for any Acceleration value and any Position value and any Temp value] for 8 seconds or more<br><br>[(HR> 160 BPM and/or RR > 30 breaths/min) and Acceleration < Medium for any Position value and any Temp value] for 8 seconds or more |

FIG. 38

Table 5. Default LSDS Alive/Normal Data Ranges

| Sensor | Parameter | Data Description (Raw Data Range) | "Normal" Range |
|---|---|---|---|
| R-Wave Detector | Heart Rate | Numeric (0 BPM, and 15 – 250 BPM) | 40 – 160 BPM |
| | Presence of Heartbeat | Boolean (T or F) | TRUE |
| Respiration Detector | Presence of Respiration | Boolean (T or F) | TRUE |
| | Respiration Rate | Numeric (0 – 60 breaths/min) | 8 – 30 breaths/min |
| | Tidal Volume Indicator (High, Medium, Low) | Integer (2, 1, 0) | High, Medium or Low |
| | Time Elapsed Since Last Breath | Numeric (0 – 60 seconds) | Not applicable |
| | Presence of Motion | Boolean (T or F) | TRUE or FALSE |
| Accelerometer | Speed (None, Slow, Medium, Fast) | Integer (0, 1, 2, or 3) | 0 - 3 |
| | Position (Upright, Horizontal, or Upside-Down) | Signed Integer (1, 0, or –1) | 0 - 1 |
| Temperature sensor | Estimated Core Temperature | Numeric (0 - 50°C) | NORMAL (36.4°C – 38.9°C) |
| | External Temperature | Numeric (0 - 50°C) | Not applicable |

FIG. 39

Table 6. Default LSDS Alive/Not-Normal Data Ranges

| Parameter | Abnormal High | Abnormal Low |
|---|---|---|
| HR | 161 and higher | 39 and lower |
| RR | 31 and higher | 7 and lower |
| Skin Temp | >39°C | <36°C |
| Acceleration | Not Applicable | Not Applicable |
| Position | Not Applicable | Not Applicable |

FIG. 40

Table 8. Default Decision Matrix for Only One Parameter in Last Decision Interval

| Parameter | Value | New State | Value | New State | Value | New State | Value | New State |
|---|---|---|---|---|---|---|---|---|
| HR | Normal | Alive | Abnormal | Alive-Not-Normal | 0 BPM | Dead | Present, can't calculate | Uncertain |
| RR | Normal | Alive | Abnormal | Alive-Not-Normal | 0 breaths per min | Dead | Present, can't calculate | Uncertain |
| Acceleration | Any | Uncertain | | | | | | |
| Position | Any | Uncertain | | | | | | |
| Temp | Any | Uncertain | | | | | | |

FIG. 41

Table 9. Default Decision Matrix for Two Parameters for Last Decision Interval

| Parameters | Average Value Range 1 | Average Value Range 2 | Average Value Range 3* | New State |
|---|---|---|---|---|
| HR and RR | Normal | Normal | | Alive |
| | Normal | Abnormal | | Alive |
| | Normal | 0 | | Alive/Not Normal |
| | Abnormal | Normal | | Alive/Not Normal |
| | Abnormal | Abnormal | | Alive/Not Normal |
| | Abnormal | 0 | | Alive/Not Normal |
| | 0 | Normal | | Alive/Not Normal |
| | 0 | Abnormal | | Alive/Not Normal |
| | 0 | 0 | | Dead |
| HR & Acceleration/Position | Normal | Any | Any | Alive |
| | Abnormal High | Fast | Any | Alive |
| | Abnormal High | Non-Fast | Any | Alive/Not Normal |
| | Abnormal Low | None | Any | Alive/Not Normal |
| | Abnormal Low | Non-zero | Any | Alive/Not Normal |
| | 0 | Any | Any | Dead |
| HR and Temp | Normal | Normal | | Alive |
| | Normal | H or L | | Alive/Not Normal |
| | Abnormal | Normal | | Alive/Not Normal |
| | Abnormal | H or L | | Alive/Not Normal |
| | 0 | Any | | Dead |
| RR & Acceleration/Position | Normal | Any | Any | Alive |
| | Abnormal High | Fast | Any | Alive |
| | Abnormal High | Non-Fast | Any | Alive/Not Normal |
| | Abnormal Low | None | Any | Alive/Not Normal |
| | Abnormal Low | Non-zero | Any | Uncertain |
| | 0 | Any | Any | Dead |
| RR and Temp | Normal | Normal | | Alive |
| | Normal | Abnormal | | Alive/Not Normal |
| | Abnormal | Normal | | Alive/Not Normal |
| | Abnormal | Abnormal | | Alive/Not Normal |
| | 0 | Normal | | Dead |
| | 0 | Abnormal | | Dead |
| Temp and Acceleration | Any | Any | Any | Uncertain |

*Note that the third value range is only filled in for acceleration (acceleration and orientation).

FIG. 42

Table 10. Default Decision Matrix for Three Parameters for Last Decision Interval

| Parameters | Average Value Range 1 | Average Value Range 2 | Average Value Range 3 | Average Value Range 4* | New State |
|---|---|---|---|---|---|
| HR, RR, and Acceleration | Normal | Normal | Any | Any | Alive |
|  | Normal | Abnormal | Any | Any | Alive/Not Normal |
|  | Normal | 0 | Any | Any | Alive/Not Normal |
|  | Abnormal High | Normal | Any | Any | Alive/Not Normal |
|  | Abnormal High | Abnormal High | Fast | Any | Alive |
|  | Abnormal High | Abnormal High | Non-Fast | Any | Alive/Not Normal |
|  | Abnormal High | Abnormal High | Any | Any | Alive/Not Normal |
|  | Abnormal High | 0 | Any | Any | Alive/Not Normal |
|  | Abnormal Low | Normal | Any | Any | Alive/Not Normal |
|  | Abnormal Low | Abnormal | Any | Any | Alive/Not Normal |
|  | Abnormal Low | 0 | Any | Any | Alive/Not Normal |
|  | 0 | Normal | Any | Any | Alive/Not Normal |
|  | 0 | Abnormal | Any | Any | Alive/Not Normal |
|  | 0 | 0 | Any | Any | Dead |
| HR, RR, and Temp | Normal | Normal | Any |  | Alive |
|  | Normal | Abnormal | Any |  | Alive/Not Normal |
|  | Normal | 0 | Any |  | Alive/Not Normal |
|  | Abnormal | Normal | Any |  | Alive/Not Normal |
|  | Abnormal | Abnormal | Any |  | Alive/Not Normal |
|  | Abnormal | 0 | Any |  | Alive/Not Normal |
|  | 0 | Normal | Any |  | Alive/Not Normal |
|  | 0 | Abnormal | Any |  | Alive/Not Normal |
|  | 0 | 0 | Any |  | Dead |
| HR, Temp, and Acceleration | Normal | Normal | Any | Any | Alive |
|  | Normal | H or L | Any | Any | Alive/Not Normal |
|  | Abnormal High | Normal | Fast | Any | Alive |
|  | Abnormal High | Normal | Non-Fast | Any | Alive/Not Normal |
|  | Abnormal High | Abnormal | Any | Any | Alive/Not Normal |
|  | Abnormal Low | Any | Any | Any | Alive/Not Normal |
|  | 0 | Any | Any | Any | Dead |
| RR, Temp, and Acceleration | Normal | Normal | Any | Any | Alive |
|  | Normal | Abnormal | Any | Any | Alive/Not Normal |
|  | Abnormal High | Normal | Fast | Any | Alive |
|  | Abnormal High | Normal | Non-Fast | Any | Alive/Not Normal |
|  | Abnormal High | Abnormal | Any | Any | Alive/Not Normal |
|  | Abnormal Low | Any | Any | Any | Alive/Not Normal |
|  | 0 | Any | Any | Any | Dead |

*Note that the fourth value range is only filled in for acceleration (acceleration and orientation).

FIG. 43

Table 11. Default Decision Matrix for Four Parameters for Last Decision Interval

| Parameters | Average Value Range 1 | Average Value Range 2 | Average Value Range 3 | Average Value Range 4 | Average Value Range 5 | New State |
|---|---|---|---|---|---|---|
| HR, RR, Temp and Acceleration | Normal | Normal | Normal | Any | Any | Alive |
| | Normal | Normal | Abnormal | Any | Any | Alive |
| | Normal | Abnormal | Any | Any | Any | Alive/Not Normal |
| | Normal | 0 | Any | Any | Any | Alive/Not Normal |
| | Abnormal | Normal | *Any | *Any | Any | Alive/Not Normal |
| | Abnormal High | Abnormal High | Any | Fast | Any | Alive |
| | Abnormal High | Abnormal High | Any | Non-Fast | Any | Alive/Not Normal |
| | Abnormal High | Normal | Any | Any | Any | Alive/Not Normal |
| | Abnormal High | Abnormal Low | Any | Any | Any | Alive/Not Normal |
| | Abnormal High | 0 | Any | Any | Any | Alive/Not Normal |
| | Abnormal Low | Normal | Any | Any | Any | Alive/Not Normal |
| | Abnormal Low | Abnormal | Any | Any | Any | Alive/Not Normal |
| | Abnormal Low | 0 | Any | Any | Any | Alive/Not Normal |
| | 0 | Normal | Any | Any | Any | Alive/Not Normal |
| | 0 | Abnormal | Any | Any | Any | Alive/Not Normal |
| | 0 | 0 | Any | Any | Any | Dead |

*Note that the fifth value range is only filled in for acceleration (acceleration and orientation).

FIG. 44

Table 12: State Change Score Components

| # of State Change Steps | Variations | Total Probability | State Change Score | Influence on Conf Score |
|---|---|---|---|---|
| 0 | G↔G, Y↔Y, R↔R | 60% | 3 | H |
| 1 | RH↔YH, YH↔G, G↔YL, YL↔RL | 30% | 2 | M |
| 2 or More | G↔RH, G↔RL | 10% | 1 | L |

FIG. 45

Table 13. Persistence Score Components

| Total # Times In New State | Score Range (Total −1) | Influence on Conf Score |
|---|---|---|
| 7 - 8 | 6 - 7 | H |
| 5 - 6 | 4 - 5 | M |
| 4 | 3 | L |

FIG. 46

Table 14. Components of Weight (Multiplier) by Parameter Set

| Parameter Included in New State | Weight (Multiplier) | Influence on Conf Score |
|---|---|---|
| All | 1.0 | H |
| HR, RR, and Motion | | |
| HR, RR, Temp | 0.9 | M |
| HR and RR | | |
| HR and Temp | 0.8 | L |
| HR and Motion | | |
| HR | | |
| RR and Temp | | |
| RR and Motion | | |
| RR | | |

FIG. 47

Table 15. Confidence Score Ranges

| Confidence Level | Score Range |
|---|---|
| High | $80 < \text{Score} \leq 100$ |
| Medium | $50 < \text{Score} \leq 80$ |
| Low | $\text{Score} < 50$ |

Block Diagram :Life Signs Detection System

LIFE SIGN DETECTION AND HEALTH STATE ASSESSMENT SYSTEM

This application is a continuation application of U.S. application Ser. No. 13/744,865, filed on Jan. 18, 2013, which is a continuation application of U.S. application Ser. No. 10/595,672, filed on Jan. 7, 2009, which is a national stage application of PCT/US04/36587, filed on Nov. 3, 2004, which claims priority to U.S. provisional application 60/517,149, the entire content of each of which is hereby incorporated by reference.

The U.S. Government has a paid-up license in this invention and the right in limited circumstances to require the patent owner to license others on reasonable terms as provided for by the terms of Army Grant No. DAMD17-02-2-2006 awarded by Department of Defense.

FIELD OF THE INVENTION

This invention relates to compact wearable systems for measuring a subject's vital signs, such as heart rate, respiration rate, temperature, position and motion, possibly processing those measurements and transmitting the results of the processing wirelessly for remote monitoring. It also relates to processing algorithms for generating electrical signals indicating vital signs, and more generally for developing diagnostic information from groups of sensor readings.

BACKGROUND OF THE INVENTION

Electronic devices for monitoring a patient's vital signs at bedside are in common use in hospitals. Typically these measure, display and transmit to nursing stations EKG traces, blood pressure values, body temperature values, respiration rates and other vitals. To accomplish this, sensors such as EKG pads, pressure cuffs, thermometers, etc. are attached to the patient by multiple leads. Each of the different devices is designed for use on a patient with limited mobility in a stable environment. In addition there are monitoring devices for heart rate, respiration and body temperature, designed for use by athletes, pilots, astronauts, etc. Some of the systems employ wireless transmission to a monitor. Again, these devices are designed for use in predictable environmental situations often where low cost and low transmission bandwidth are not limiting factors. These devices for the most part report detailed data such as full EKG trace details, although some merely have alarm functions if certain parameters are exceeded.

There has long been desired a reliable, reasonably low cost system for monitoring and aiding in the triaging of wounded soldiers in a battlefield environment, or triaging multiple trauma victims at an accident site. In particular the devices do not exist that could be worn by a soldier in the chaotic battlefield environment to provide enough useful information on vitals to say with confidence that the soldier is beyond the point where medical intervention would be useful, so as to be able to avoid or terminate rescue attempts that place a rescuer's life in jeopardy. Thus medics and other rescue personnel continue to be killed or seriously injured attempting to rescue soldiers where rescue was already hopeless. Despite the great need for systems to avoid such unnecessary casualties there has heretofore been no satisfactory system economical enough to simultaneously monitor large numbers of armed forces.

Such a system would also obviously be useful in non-military chaotic situations. For example ambulances and emergency vehicles are often equipped with personnel and diagnostic equipment that can be overwhelmed in situations where there are several injured to treat simultaneously. Again, there is not available at reasonable cost health assessment systems that could be applied to multiple subjects to allow triaging to take place rapidly by persons remote from the scene of injury.

Suggestions have been made as to how such systems should be organized and what should be measured. Nevertheless, despite these suggestions and the great need, the prior art has not advanced to the point where such systems have been built and made practical.

Prior patents that may relate to the problems of health state assessment are the following:

Respiration Effort Sensors

U.S. Pat. No. 5,513,646 entitled "Personal Security Monitoring System and Method" discloses a breath detector and a signal processor where the signal processor distinguishes between the user's normal breathing patterns and other patterns that trigger alarms.

U.S. Pat. No. 5,611,349 entitled "Respiration Monitor with Simplified Breath Detector" discloses a pneumatic breath detector using a low pass filter to reduce signals not indicative of respiration.

U.S. Pat. No. 6,377,185 entitled "Apparatus and Method for Reducing Power Consumption in Physiological Condition Monitors" discloses using a high power mode when data is written and a low power mode when inactive. Incoming data is placed in a low power buffer and transferred in a single data transfer.

U.S. Pat. No. 5,331,968 entitled "Inductive Plethysmographic Transducers and Electronic Circuitry Therefor" discloses such a device where the circuitry is located remotely rather than on a transducer.

U.S. patent application 2002/0032386 entitled "Systems and Methods for Ambulatory Monitoring of Physiological Signs" discloses monitoring apparel with attached sensors for pulmonary and cardiac function by including ECG leads and a plethysmographic sensor. Data from the sensors is stored in a computer readable medium for later use by health care providers.

Sensors and Signal Processors for Extracting a Physiological Measurement, Especially in a High Noise or High Motion Environment U.S. Pat. No. 6,520,918 entitled "Method and Device for Measuring Systolic and Diastolic Blood Pressure and Heart Rate in an Environment with Extreme Levels of Noise and Vibrations" discloses using an acoustic sensor on the patient near an artery and a second acoustic transducer away from the artery. The signal of the first sensor is processed using an adaptive interfere canceller algorithm with the signal of the second acoustic sensor as interferer.

U.S. Pat. No. 6,629,937 entitled "System for Processing Audio, Video and Other Data for Medical Diagnosis and Other Applications" discloses a system for storing acoustic data in a file associated with a patient's medical record, which are analyzed to determine physiologically significant features useful in medical diagnosis based on an automatic analysis.

U.S. Pat. No. 5,853,005 entitled "Acoustic Monitoring System" discloses a transducer that monitors acoustic signals representative of heartbeat or breathing and transferred into a fluid. A comparison is made with predetermined reference patterns.

U.S. Pat. No. 6,616,613 entitled "Physiological Signal Monitoring System" discloses a system for determining blood pressure, heart rate, temperature, respiratory rate, and arterial compliance on the basis of signal characteristics of the systolic wave pulse. The systolic reflected wave pulse contour is subtracted from the digital volume pulse contour.

U.S. Pat. No. 6,200,270 entitled "Sensor for Non-Invasive and Continuous Determination of the Duration of Arterial Pulse Waves" discloses two spaced apart piezoelectric pressure sensors along the artery.

Wireless Networks—Low Power Digital Data Networks in the "Body Area" or "Personal Area" Space; Selectable Data Rates, Data Buffering and Store and Forward Means U.S. Pat. No. 6,577,893 entitled "Wireless Medical Diagnosis and Monitoring Equipment" discloses wireless electrodes attached to the surface of the skin of a patient and having a digital transmitting and receiving unit.

U.S. Pat. No. 5,755,230 entitled "Wireless EEG System for Effective Auditory Evoked Response" discloses an electrode array for attachment to a person that senses voltages produced by brain electrical activity. An operator interface records a verbal stimulus and provides a comparison of the brain activity with the stimulus.

U.S. Pat. No. 6,167,258 entitled "Programmable Wireless Data Acquisition System" discloses such a data collecting system where a transmitting device can receive multiple inputs and transmit a signal encoded with data corresponding to the inputs.

U.S. Pat. No. 6,223,061 entitled "Apparatus for Low Power Radio Communications" discloses such a system controlled frequency modulation where a phase lock loop synthesizer is set to an open loop state to allow FM unimpeded by the normal frequency correcting action of the synthesizer.

U.S. patent application 2002/0091785 entitled "Intelligent Data Network" provides two-way communication between a node and a master device by pausing to listen after each transmission.

U.S. Pat. No. 6,450,953 entitled "Portable Signal Transfer Unit" discloses a system for relaying physiological data employing a memory for buffering the signal and wirelessly transmitting it to a remote unit.

U.S. Pat. No. 6,454,708 entitled "Portable Remote Patient Telemonitoring System Using a Memory Card or Smart Card" discloses a system that records full waveform data on smart cards. The system uses cordless, disposable sensors.

Systems for Remote Monitoring of Personnel

U.S. Pat. No. 6,579,231 entitled "Personal Medical Monitoring Unit and System" discloses a portable unit worn by a patient that stores physiological data and issues medical alarm conditions via wireless communications. The unit works with a central reporting system for long term collection and storage of the subjects data and can automatically dispense chemicals.

U.S. patent application 2002/0019586 entitled "Apparatus for Monitoring Health, Wellness and Fitness" discloses two sensors coupled to a processor and a memory for storing the data, which is subsequently transmitted.

U.S. Pat. No. 6,605,038 entitled "System for Monitoring Health, Wellness and Fitness" discloses a sensor worn on the upper arm including an accelerometer, GSR sensor and heat flux sensor. A central monitoring unit generates analytical status data that is transmitted to a recipient.

U.S. Pat. No. 6,160,478 entitled "Wireless Health Monitoring System" discloses a system for remotely monitoring a person's physical activity through use of an accelerometer. It may be used to determine whether a person has fallen and the likely severity of the fall and trigger an alarm.

U.S. Pat. No. 6,611,206 entitled "Automatic System for Monitoring Independent Person Requiring Occasional Assistance" discloses monitoring independent signals and combining them into a single alarm for possible intervention by a supervisor.

U.S. Pat. No. 6,198,394 entitled "System for Remote Monitoring of Personnel" discloses sensors disposable on a soldier that communicate with a soldier unit that can process the information to ensure that it falls within acceptable ranges and communicate with remote monitors. Body surface and ambient temperature are monitored. The inflammation may be stored and kept with the soldier to enable improved care as the soldier is moved to higher levels of care.

U.S. Pat. No. 6,433,690 entitled "Elderly Fall Monitoring Method and Device" discloses a system for recording acceleration and body position data from elderly or disabled persons. It detects health and life threatening falls and notifies nursing personnel of the need for assistance.

U.S. Pat. No. 6,416,471 entitled "Portable Remote Patient Telemonitoring System" discloses a system for transferring the full waveform ECG, full waveform respiration, skin temperature and motion data to a transfer unit worn by the patient on a belt for subsequent transfer to a monitoring base station where clinical data can be compared against given profiles.

U.S. Pat. No. 6,559,620 entitled "System and Method for Remote Monitoring Utilizing a Rechargeable Battery" discloses using such a battery in a system for remotely monitoring a person's position by GPS satellite.

Wearable Physiological Sensor Arrays and Processing Means Therefor (Vests, Straps, Adhesive Arrays, Etc.)

U.S. Pat. No. 6,527,711 entitled "Wearable Human Physiological Data Sensors and Reporting System Therefor" discloses a series of rigid and flexible pods within which sensors and computing apparatus are housed. The system allows relative movement of the rigid sections with respect to each other.

U.S. Pat. No. 6,494,829 entitled "Physiological Sensor Array" discloses a system for transmitting sensor output. Respiration is detected by a bend sensor.

U.S. patent application 2003/0105403 entitled "Wireless ECG System" discloses a cardiac monitor for a patient that transmits signals digitally to a remote base station, which converts the signals back to analog electrical signals to be read by an ECG monitor.

Sensors for Use in Physiological Monitoring (Temperature, Body Position, Blood Pressure, EKG or Heart Rate), Especially Under Exercise Conditions U.S. Pat. No. 5,168,874 entitled "Wireless Electrode Structure for Use in Patient Monitoring System" discloses a wireless patient monitoring system using a patch electrode having a micro-chip amplifier on one side of the patch electrode.

U.S. Pat. No. 5,622,180 entitled "Device for Measuring Heartbeat Rate" discloses a wrist strap with skin contact electrodes such that signals from a skin sensor are filtered and pulse shaped for display.

U.S. Pat. No. 5,976,083 entitled "Portable Aerobic Fitness Monitor for Walking and Running" discloses a system for calculating the fitness of a person using personal data and comparing that data to pedometer and heart rate values generated during exercise.

U.S. Pat. No. 4,566,461 entitled "Health Fitness Monitor" discloses a heart rate monitor for use in aerobic exercise that calculates a fitness parameter by monitoring heart rate as the subject paces through an exercise stress test protocol. The system emits beeps that the subject matches to its stride frequency. At the point of exhaustion the maximal oxygen uptake capacity is determined and is displayed.

U.S. Pat. No. 5,544,661 entitled "Real Time Ambulatory Patient Monitor" discloses a patient monitoring system including an ECG and a photo-plethysmograph, arrhythmia analysis apparatus and an expert system for determining if a pre-established critical parameter set has been exceeded. When alarmed the ECG waveform and trends are transmitted to a clinician.

U.S. Pat. No. 6,236,882 entitled "Noise Rejection for Monitoring ECGs" discloses a looping memory for storing triggered physiologic events (such as arrhythmias and syncopal events) with auto triggers to record the ECGs. Denial and extensible accommodation periods are introduced in the R-wave sensing registration for triggering data storage.

U.S. Pat. No. 5,743,269 entitled "Cardiotachometer" discloses a system for computing a heart rate from ECG signals and encoding the signals for transmission to avoid erroneous reception of signals generated by noise or interference.

BRIEF DESCRIPTION OF THE INVENTION

A system makes health state assessments based on data from a wearable platform embodied in a belt or patch that provides physiological monitoring of soldiers during field operations or trauma victims at accident sites. The system is the first capable of making a determination of the health state of the wearer with sufficient confidence to base triage decisions on that determination as opposed to merely reporting vital sign data. The system, in addition to sensors of vital signs and telemetry, has a rule processing engine, comprising a microprocessor running a health state assessment algorithm. It makes a health state assessment based on the remarkable determination that for an individual who is monitored in real time for at least one significant vital sign (e.g., heart rate, ECG waveforms, SpO2, respiration rate) and possibly one or more indirect life signs (such as body movement or response to direct command), it is possible to determine, with reasonable accuracy, whether the person is alive or dead. With an appropriately rich set of direct and indirect life signs, it is possible to further estimate the likelihood of injury or even the nature of an injury for such applications as remote triage.

The system makes a health state assessment of a subject at a location remote from a clinician based on indications of vital signs together with a simulation of an on site assessment of the subject. In place of the visual observations that would be part of an on site assessment of the subject, sensors provide indications of indirect life signs such as movement, orientation and position. These indications of vital signs and indirect life signs are input to rule sets implemented in a rule processing engine executing a health state assessment algorithm.

The rule sets may be varied depending upon the general characteristics of the subject population. Such populations may range from healthy young soldiers to elderly overweight individuals. The rule sets may be changed at different levels. At the highest level, typically attended by a clinician, the changes may comprise the inclusion or removal of parameters for particular indications. At a lower level of clinical support, the changes may comprise changing the range or interpretation afforded the values of the different parameters. The system accommodates parameter values that do not correspond to numeric values, such as whether a motion fits the categories of slow, medium or fast, or indicates that a shock has occurred outside the scale of any such motion. The various rule sets may be achieved by simulating the experience of skilled health professionals.

A feature of the invention is the integration achieved between the various components. The respiration sensor for example may sense abdominal motion and thus also gives information on motion of the subject, which supplements the information provided by an accelerometer sensor. Thus there is a synergistic relation among the various sensor components and with processor elements. All of the sensor information is assimilated by a health state assessment algorithm (HSAA) that is capable of making a medical evaluation of a subject's condition and determining a confidence level for the evaluation.

The system of the invention is referred to as the Life Signs Detection System (LSDS) since one of its functions is to determine with confidence whether a warrior is alive. The wearable platform preferably includes sensors for heart rate, body motion, respiration rate and respiration intensity, and temperature and further contains a microprocessor and short range transmitter. A separate wearable package that would be expected to be carried by a soldier for other communication purposes contains a local transceiver hub that receives signals from the short range transmitter and transmits the signals more remotely.

Data received from the various sensors are processed in a microprocessor to produce a simplified, low-bandwidth output. The output is transmitted from the wearable package by a short range RF transmitter contained within the unit.

An additional component, called the Local Hub, is also worn by the subject. In its simplest form the local hub contains a short range RF transceiver, a medium or long range RF transmitter or transceiver, and a microprocessor. The local hub receives the transmitted data from the LSDS wearable package and retransmits the signals to a remote station or base station. Retransmission is not necessarily synchronous with reception; the microprocessor may perform additional processing on the received data, may store the received data for later transmission, may add information to the data, and may reconfigure the data for more efficient transmission or other reasons (e.g. increased security or privacy).

A sensor subsystem is responsible for conversion of one or more hardware biologic indicators into a periodic digital data packet. This data packet will be transmitted over a local, low-power RF link to the hub, at an appropriate data rate. Alternately, but less preferably, the sensors could rely on ND conversion in the hub.

A hub subsystem is responsible for collection of all the local sensor data, performing additional data analysis if needed, and relaying the information to the remote station. The hub subsystem is responsible for recognizing and maintaining association to a specific set of sensor subsystems, so that data from other sensors that are physically proximate, but are monitoring a different person will not get mixed in. The hub subsystem is responsible for providing periodic and/or on-demand advertisement of its availability and status, and to accept a connection from one or more external display or other systems.

A remote subsystem is responsible for collecting data from multiple hubs, for example up to 20 hubs, and displaying them on a normal-sized laptop or portable computer screen.

A medic PDA subsystem used in lieu of or in addition to the remote station is responsible for providing the detailed data display for a selected hub.

Processing of signals takes place at various levels within the electronics worn by the subject. The levels are:

1. Original Signal—The raw, unprocessed signal generated by a sensing element.
2. Preparation—Basic analog processing, including amplification, applied to the signal to make it usable for later processes.
3. Storage (optional)—Retention of digital values for possible later use.
4. Feature Extraction—Analog and/or digital processing of the signal to obtain recognition of basic signal features such as frequency and amplitude.
5. Scoring—Digital processing to determine metrics of extracted features such as averages, trends, and bin (level) counts.
6. Evaluation—Digital processing of data to determine overall conditions, access whether data is within normal ranges, and to generate warnings or alarms.
7. Extended Evaluation—Intensive digital processing to correlate multiple signals or multiple subjects, access the quality of received data and signals, and to perform complex feature extraction.

The invention thus provides a health state assessment rule processing engine, comprised of algorithms that estimate physiologic state and decision confidence by applying one or more medical determination "rule sets" to data received from the sensor array and from any clinician input devices in the system. Medical determination rule sets consist of decision logic and related parameter limit ranges tailored to a subject's health category. Examples of health categories include "healthy adult", "Congestive Heart Failure (CHF) patient", and "subject's personal health baseline." The default rule set for the algorithm is the healthy adult category. Data from clinician input devices is optional, and consists of information observed on-site, such as "ballistic injury to limb."

The assessment of physiologic state may be limited to good/weak/poor determinations of health given the default sensor array that detects heart rate, respiration rate, activity/orientation, and temperature. With an extended sensor array (for example, by adding blood pressure and oximetry), the assessment may be as comprehensive as normal/needs attention/critical determinations of health, along with continuous "remote triage" indicators (such as "high likelihood of shock").

Other objects of the invention will be apparent from the following detailed description of the invention.

BRIEF DESCRIPTION OF THE DRAWINGS

FIG. 9 is a drawing of a flex sensor element.
FIG. 10 is a drawing of a flex sensor mounted to a support.
FIG. 34 is Table 1: LSDS Platform Parameters and Error Conditions
FIG. 35 is Table 2: Default Health State Classification Descriptions
FIGS. 36A and 36B are Table 3: Default Life Signs Interpretation Rules for Alive/Green and Dead/Red States
FIG. 37 is Table 4: Default Life Signs Interpretation Rules for Alive/Yellow State
FIG. 38 is Table 5: Default LSDS Alive/Normal Data Ranges
FIG. 39 is Table 6: Default LSDS Alive/Not-Normal Data Ranges
FIG. 40 is Table 8: Default Decision Matrix for Only One Parameter in Last Decision Interval
FIG. 41 is Table 9: Default Decision Matrix for Two Parameter Over Last 16 Decision Interval
FIG. 42 is Table 10: Default Decision Matrix for Three Parameters in Last Decision Interval
FIG. 43 is Table 11: Decision Matrix for Four Parameters in Last Decision Interval
FIG. 44 is Table 12: State Change Score Components
FIG. 45 is Table 13: Persistence Score Components
FIG. 46 is Table 14: Components of Weight (Multiplier) by Parameter Set
FIG. 47 is Table 15: Confidence Score Ranges

DETAILED DESCRIPTION OF PREFERRED EMBODIMENTS OF THE INVENTION

Figure 1:
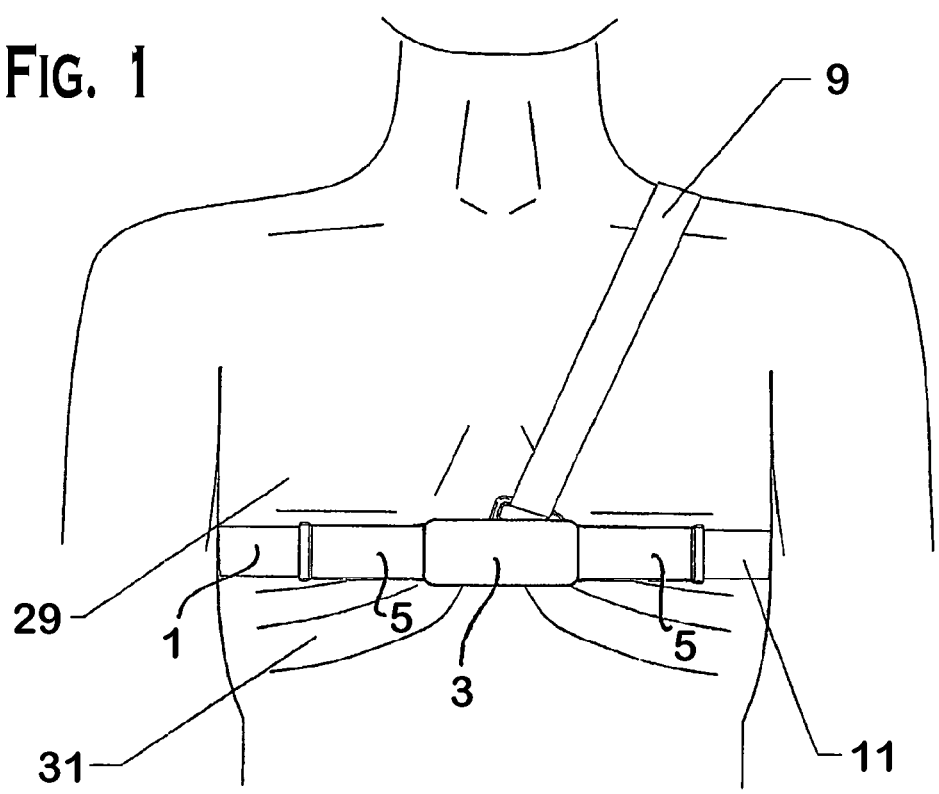
FIG. 1 is a drawing of the LSDS worn by its subject.
Figure 3:
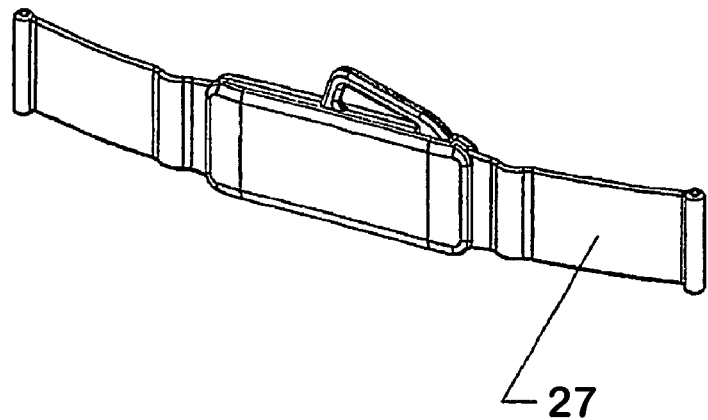
FIG. 3 is a perspective drawing of the central housing and extensions view from the front.

As shown in FIG. 1, the Life Signs Detection System (LSDS) comprises an apparatus containing a group of sensors for certain vital physical parameters of a subject person and electronics to receive and interpret electrical signals from the sensors, process the signals and transmit information on the physical status of the subject. The group of sensors and electronics is embodied in a carrier 1 arranged to be worn by the subject.

The electronics residing on a PC board is designed to accomplish most signal processing at the location of the subject and to avoid the need for robust networking and centralized computing that require large amounts of bandwidth to transmit raw signals for analysis.

Such large bandwidth is impractical in field settings where bandwidth is loW, unreliable and localized responsiveness must be maintained.

Health State Assessment Algorithm

The clinical health state assessment algorithm for use in the LSDS combines raw data collected by the LSDS sensors to determine the following information:
  Physiologic State—Physiological data acquired and analyzed to classify general wellness and rule out a physiologic state consistent with death
  Decision Confidence Score—A calculated indicator of diagnostic certainty of the physiologic state classification
  Multi-Tier Processing—Using a revisable rule set, physiologic state and confidence score are calculated using a rules set based on one's personal baseline
  Triage Indicators —Acquire, analyze, and report appropriate collection of life sign parameters to support specific diagnostic assessments.

The rules processing engine makes continuous health state assessments based on the multiplicity of current and trended sensor inputs and clinician inputs, as defined by the rule sets in use. Table 1 lists the default data available from the monitor's sensors for use in the processing engine, along with associated error conditions. A medical determination rule set for the processing engine must include the medical decision logic to produce the following minimum information based on continuous processing of raw sensor data:
  A color-coded health state classification (green for alive and normal, yellow for alive and not normal, red for critical or dead)
  An indicator of extent of confidence in the accuracy of the health state classification (i.e., "diagnostic certainty").

At least one rule set (the "primary rule set") must be available to the rules processing engine. If more than one rule set is available, multi-tier processing can occur. This is particularly desirable when more than one type of decision must be made for the monitored patient. For example, for a soldier monitored on the battlefield the primary rule set allows remote decision-makers to determine that a soldier is alive but injured, and that a medic needs to be dispatched. A second tier of decisions would be useful to aid the dispatched medic in preparing to treat the injured soldier (for example, which medication and equipment are indicated). A rule set that is not "primary" can be configured to be continuously "active" or to be activated and deactivated on demand from a remote clinician input device.

Data trending for the rules processing engine is performed continuously for each parameter in the sensor array and for any numeric parameter provided via the clinician input device. A parameter trend is predefined (e.g., an average, a minimum or a maximum) for a fixed time interval ("decision interval"). The decision interval is based on the minimum amount of time a clinician would observe a patient's real-time physiological data before making a clinical decision based on that parameter. The default decision interval for the rules processing engine is sixteen (16) seconds. Thus with each new set of inputs from the sensor array (the default is once every two seconds), the monitored data is trended for the most recent sixteen (16) seconds (that is, the current two (2) seconds of data and the previous fourteen (14) seconds of data).

Health State Classifications

Table 2 defines the default health state classifications (e.g. alive, abnormal, dead, uncertain) and associates them with a color code that will be available to remote or onsite clinicians. That is, the color code will be displayed at remote assessment stations and on portable clinician input/display devices (such as PDAs).

Confidence Score

The confidence score represents level of confidence in the accuracy of a given health state decision. The calculation for confidence score is based on the probability (percentage of likelihood) that a given health state assessment (Green color code, Yellow color code, or Red color code) is accurate.

Life Signs Data Prioritization

Data prioritization is used to determine the order for proceeding through the processing engine's data interpretation rules. Prioritization provides an abstraction of the order in which an on-site clinician would examine life signs data. Prioritization also allows a "value level" to be assigned to individual life signs (from "high value" to "low value") as an indication of usefulness in determining health state. The value level is considered in computing a confidence score for each health state assessment decision.

The default LSDS data prioritizations are as follows, based on clinical usefulness of each parameter compared to the traditional vital signs monitoring scenario, which includes visual patient inspections.
  1. Heart Rate—Numerical, traditional measurement of heartbeat; high value
  2. Respiration Rate—Numerical, traditional measurement of breathing; high value
  3. Speed of motion (None, Slow, Medium, or Fast), substitutes for visual observation of activity (e.g., Fast might be assumed to equal running, and can be used to justify high heart rate); medium value
  4. External Body Temp—Skin temperature influenced by ambient temperature (weather, garments, etc.); correlation to core temperature (traditional measurement). Skin temp can be useful in remote assessment situation where the monitored individual's environmental conditions are known to assessment personnel (or post-processing software). Low value.
  5. Position of body—substitutes for visual observation of standing or lying down; (e.g., sleeping could result in position of lying down, along with slowed respiration rate and speed of motion at NONE); low value Interpretation Rules for "Green" and "Red" Health States This section lists the default interpretation rules to support the decisions for the Alive/Green-Normal and Dead/Red states. The Alive/Yellow-Not-Normal state and the Uncertain/Blue states are addressed in separate sections below. Each rule is stated in terms of specific life sign parameters (breadth of data) and length of observation time (duration of monitoring).

Table 3 is based on medical judgment for the default "healthy adult" population and summarizes the rules implemented in the processing engine that apply to current Alive/Green and Dead/Red states.

Interpretation Rules for Alive/Yellow State

Given the default life signs data available from the LSDS sensor platform, the Alive/Yellow-Not-Normal state indicates that at least one "high value" parameter, either HR or RR, is outside the normal range for a sustained time interval. Table 4 lists the default interpretation rules that support the decisions for the Alive/Yellow-Not-Normal state. Again, this is based on medical judgment for a "healthy adult" population.

Interpretation Rules for Uncertain/Blue State

The default Uncertain/Blue color code state is defined by all combinations of parameter values not covered in Tables 3 and 4.

Algorithm Boundary Conditions

This section describes the default boundary conditions applied to the LSDS health state assessment algorithm for the "healthy adult" population.

"Normal" Data Ranges

Table 5 lists the data ranges that define the highest and lowest values each default LSDS sensor can calculate (see Data Description column) and the default "Normal" data ranges for the "healthy adult" population.

Abnormal High and Abnormal Low Data Ranges

For the LDSD sensor platform 1, the default ALIVE/YELLOW state is characterized by the following conditions persisting over an appropriate time interval:

- HR is outside of normal range (non-zero, higher or lower than normal range)
- RR is outside of normal range (non-zero, higher or lower than normal range)
- "History" data (trend) indicates a rate of change of physiological state that correlates with certain know injury conditions (e.g.; exsanguination)
- Absolute external temperature is not below 36.4° C. and not above 38.9° C.

The resulting abnormal data value ranges for heart rate (HR), respiration rate (RR) and skin temperature are shown in Table 6.

Algorithm Details

The algorithm involves two to three sequential steps that are repeated for each decision interval (a default of the most recent 16 seconds, in the case of the LSDS sensor platform), each time a new data packet is received (every two seconds, in the case of the LSDS monitor), and for each tier of processing in use. The steps are as follows:

- Translate sensor data and any clinician inputs into health state decisions—Based on the valid sensor data, clinician inputs received in the most recent decision interval, and resulting trended data, find the appropriate decision rule and corresponding implied health state color code for each active rule set.
- Estimate the "goodness" of the new decision—Based on the likelihood of the new state transition (previous state compared to new state), the persistence in the new state and the number and priority of parameters received for the new state, produce an appropriate confidence score.
- Optionally, identify specific triage indicators—If an extended sensor array is available, including at least a blood pressure measurement, find and report specific triage characteristics that indicate abnormal or critical health states.

Note that me multi-tier nature or me algorithm lies in its ability to apply multiple rule sets continuously, or on demand (from a remote assessment device). Additional rule sets, such as one's own personal health baseline rules, can be processed in the on-body monitoring device or on the remote assessment device.

Processing of triage indicators relies on a triage-specific rule set. Thus the rules processing engine functions the same for health state and triage indicators. The difference is in that triage reporting includes literal "indicators" and explicit related parameter values, whereas, health state is reported as a color code.

(Table 7 intentionally omitted)

Translate Sensor Data to a Health State Decision

The default rules set for the LSDS monitor have been restated in decision matrices (Tables 8-11) that correspond to the number of parameters received in a decision interval. Note that, although the default rules set primarily uses 8 seconds of sensor data for state determination, the algorithm defaults to a 16-second decision interval. This is because the physicians' rules for assessing healthy adults are based on the availability of continuous physiological data in traditional monitors, typically eight or more data samples at 1-second intervals. The algorithm's default 16-second interval is an effort to increase the likelihood of having at least 8 data samples from the LSDS monitor, which delivers data at 2-second intervals.

Red State Exceptions

For the default rule set these critical red states exceptions take priority over all other state decisions, regardless of the presence of other valid parameters:

- If HR=0 for 4 minutes or more, New state=RED, and Confidence Score=100
- HR<30 BPM for 10 minutes or more, New state=RED, and Confidence Score=100
- RR=0 for 5 minutes or more, New state=RED, and Confidence Score=100

Confidence Score

The confidence score is a value of 100 or less rounded to one decimal place, with 00 as the highest possible confidence score. A score below 50 indicates a low confidence level, from 50 to below 80 indicates a medium confidence level, and 80 or above indicates a high confidence level. This is summarized in Table 15. The score is calculated as follows:

$$\text{Confidence score} = 10 * [\text{parameter set weight} * (\text{state change score} + \text{persistence score})]$$

There are three components to the confidence score:

State change score—This score reflects the likelihood of the observed state change State persistence score—The number of times the new state was previously observed in sequence Parameter set weight—A multiplier intended to reflect the breadth of the most recent set of available parameters State Change Score State change score is a reflection of the likelihood of going from one health state to another. The underlying probabilities are based on the following assumptions:

- Vital signs activity tends to stabilize after a sustained period in a given level of activity for normal healthy adults
- The sensor platform captures data quickly enough to expect health state changes to typically occur in no more than one step at a time
- State changes of two or more steps are likely to reflect critical wounding. In the absence of actual data for likelihood of a soldier being wounded, a rough estimate was used to determine that probability Table 12 describes the components of the state change score.

State Persistence Score

The confidence score factors in the amount of time that the health state does not change. As stated earlier, vital signs activity tends to stabilize after a sustained period in a given level of activity for normal healthy adults. Therefore, the algorithm assumes that persistence of a green, red, or yellow state improves the likelihood that the sensor data and resulting health state assessment are correct.

Persistence reflects number of times the current data was previously observed during the decision interval (default of the most recent 16 seconds, 8 data samples). Thus the maximum value for persistence score is 7, and the minimum value is 0.

Table 13 describes the component of the persistence score. Table 14 relates the persistence score to High, Low, and Medium influence of state persistence on the overall confidence score.

Parameter Set Weight

The parameter set weight is an indicator of the number and importance of the parameters used to make the health state assessment. Table 14 describes the components of the parameter set weight.

Description of the Physical Carrier

Figure 2:
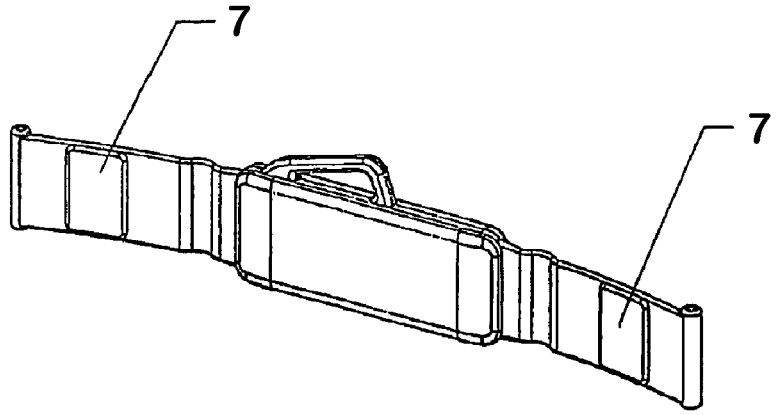
FIG. 2 is a perspective drawing of the central housing and extensions viewed from the back side.

The carrier comprises three main elements—a central housing 3, two flexible extensions 5 containing external sensors 7 (see FIG. 2), and a harness 9. The LSDS package is intended to be worn underneath the subject's clothing with the housing positioned approximately over the solar plexus. It is held in place by an elastic harness that consists of one strap (belt) that passes around the subject's back and another that passes over the left shoulder. The two flexible extensions 5 protrude from the sides of the housing and form the connections to the horizontal strap 11 of the harness.

Respiration Sensors

Figure 4:
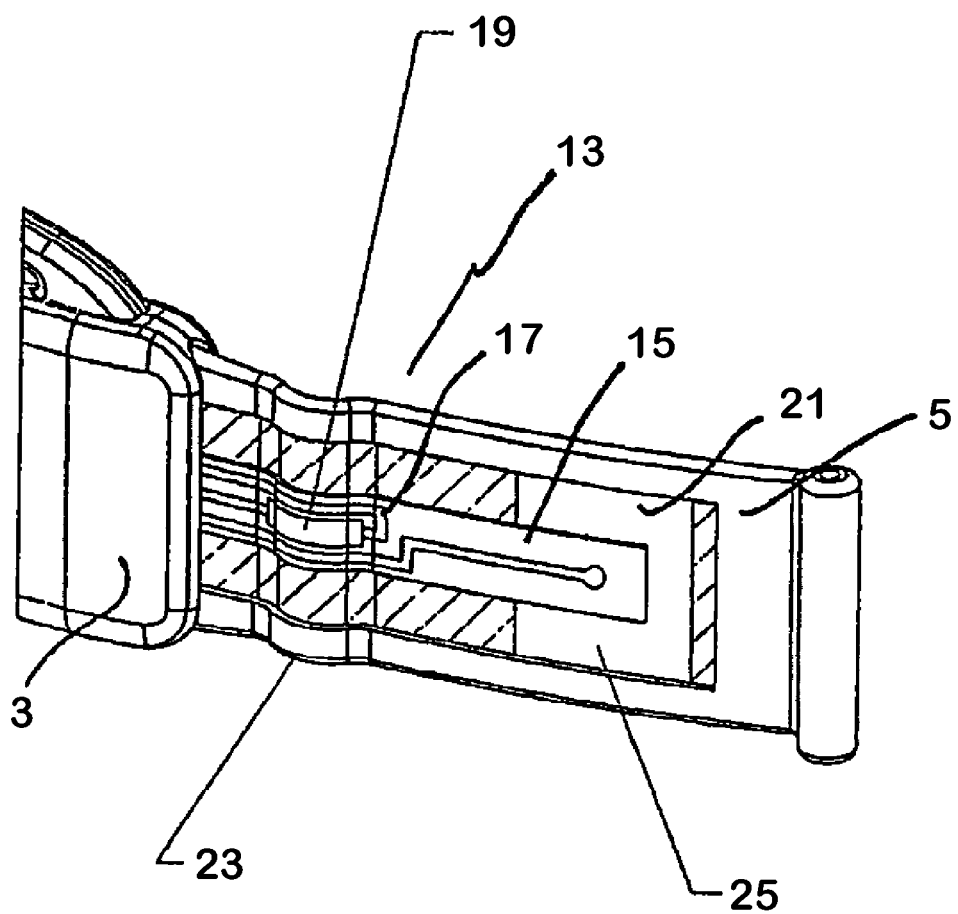
FIG. 4 is a cut away drawing of the extension and flex sensor.

Respiration sensors 13 (FIG. 4) are used in connection with an electronic circuit to provide a signal indicative of body motions accompanying respiration. They comprise a strip of flexible film material 15 that is overprinted with conductive leads 17 connecting—to a small (millimeter dimensioned) area of resistive material having the property that its resistance increases as the strip is flexed convexly. The sensor is laminated using a thermal adhesive to a thicker base layer 21. The two are then thermoformed so that the center of the strip (containing the small resistive area) is shaped into an arch 23 while the ends 25 remain flat. Small rectangles of fabric are mounted to the flat ends using a thermal adhesive; this provides a means for sewing the sensor securely to the housing extensions. Grommets or rivets are added to the sensor so that wires can be soldered in place to connect to the PC board.

Each respiration sensor is sewn to the front surface of one of the housing extensions 5, aligned along the extension. The fabric of the extension is pushed together slightly under the arched section so that the tension load when worn will be mainly across the sensor. The nylon cover material 27 is split so that the center of the sensor is uncovered, both to make it visible and to allow for greater compliance. The term "compliant" is used here to mean elastically deformable or spring-like, as opposed to the extremes of either rigid or completely flexible.

FIG. 1 shows the manner in which the configuration here described is worn be the subject. The complete assembly of central housing and extensions 3 is attached at both ends to an elastic strap that wraps tightly around the subject's back, holding the components tightly against the skin and placing a tensile load across the respiration sensor. An optional shoulder strap 9 prevents the assembly from slipping down during physical activity. The assembly is preferably placed in a horizontal alignment below the lower edge of the pectoral muscle 29 and crossing over the lower ribs 31. This area undergoes a large degree of expansion and contraction during respiration and causes respective increases and decreases in the tension across the sensors, thus producing changes in resistance.

EKG Sensors

EKG sensors are pads 7 of conductive rubber wired to the electronic circuit of the LSDS contained on a PC board within the central housing 3 together with the battery. They are sewn to the back of the housing extensions so that they will be in direct contact with the wearer's skin. A small wire (not shown) is threaded into the rubber and connected to a longer wire (or other pathway) to create an electrical connection to the PC board. The wire is attached so that it will not come into contact with the wearer's skin.

Another, more mass producible embodiment of the LSDS is similar in form, but this alternative design includes the following features:

1. The housing extensions are fabricated from an injection molded elastomer. The respiration sensors and EKG electrodes (also molded) are embedded into the housing extensions using a combination of multi-shot molding and mold-in-place techniques. Sealing lips are molded into the ends of the housing extensions that fit into the housing.
2. The housing is injection molded and is assembled using either solvent bonding or ultrasonic welding rather than screws. This provides both increased strength and a water-tight seal. Contacts for the battery charger may be molded into the case.
3. The rear half of the case may be molded from a flexible material for greater comfort. Alternatively, a pad, cover, or coating of a soft, textured material may be applied to the outer surface of the rear half of the case.
4. The harness (not shown) may be formed from an elastic material that does not have the Velcro "loop" surface but does present a soft, textured surface against the skin. Velcro or other types of adjustable devices may be attached to the strap ends to make them adjustable and removable.
5. Due to resilience of the straps, the EKG electrodes are able to remain in contact with the same portion of skin as the subject breathes, and moves (as in walking, etc.), rather than having the electrodes slide over the skin. This significantly reduces the surface resistance where the skin and the electrode are in contact.

The Respiration Flex Sensor

The respiration sensor thus employs a novel deformation transducer element 19 that varies in electrical resistance as the chest or abdomen expands and contracts due to respiration. The respiration sensor provides relatively high signal levels that can easily be interfaced to a recording or transmitting component.

The novel transducer of the flex sensor is employed to produce an electrical resistance that varies with applied tensile, compressive, or bending loads. The basic structure consists of a flexible, variable resistance element 19 and a compliant backing or support element 21. The resistance of the flexible element increases as its radius of curvature decreases. It has a minimum resistance value when flattened. Two such elements are arranged on the extension so that each flexible element has a preset curvature when no load is applied. A tensile load while taking a breath will tend to reduce the curvature, thus decreasing the resistance; a compression load will act oppositely. Bending loads will similarly cause the resistance to increase or decrease depending on the direction of flexure. The backing or support element acts as a spring and limits the degree of deformation of the flexible element. This results in the change in resistance being approximately proportional to the applied load.

Respiration Tension Sensor

Various structures could be used to hold the transducer against the subject to detect respiration or other motion. The transducer means may be employed in one of several configurations. In one configuration it is employed as a tension sensor. The transducer is mounted to an elastic strap 11 such that the transducer is subjected to the full tensile load applied when the strap is stretched along its length. The strap, which is formed into a belt that fits around the chest or abdomen of the subject, is fabricated or adjusted to a length that insures that it will always be loaded in tension as the subject breaths or moves about. As the subject inhales and exhales the tension on the strap increases or decreases correspondingly. This creates a corresponding change in the electrical resistance of the transducer as described above.

Respiration Bending Sensor

Figure 5:
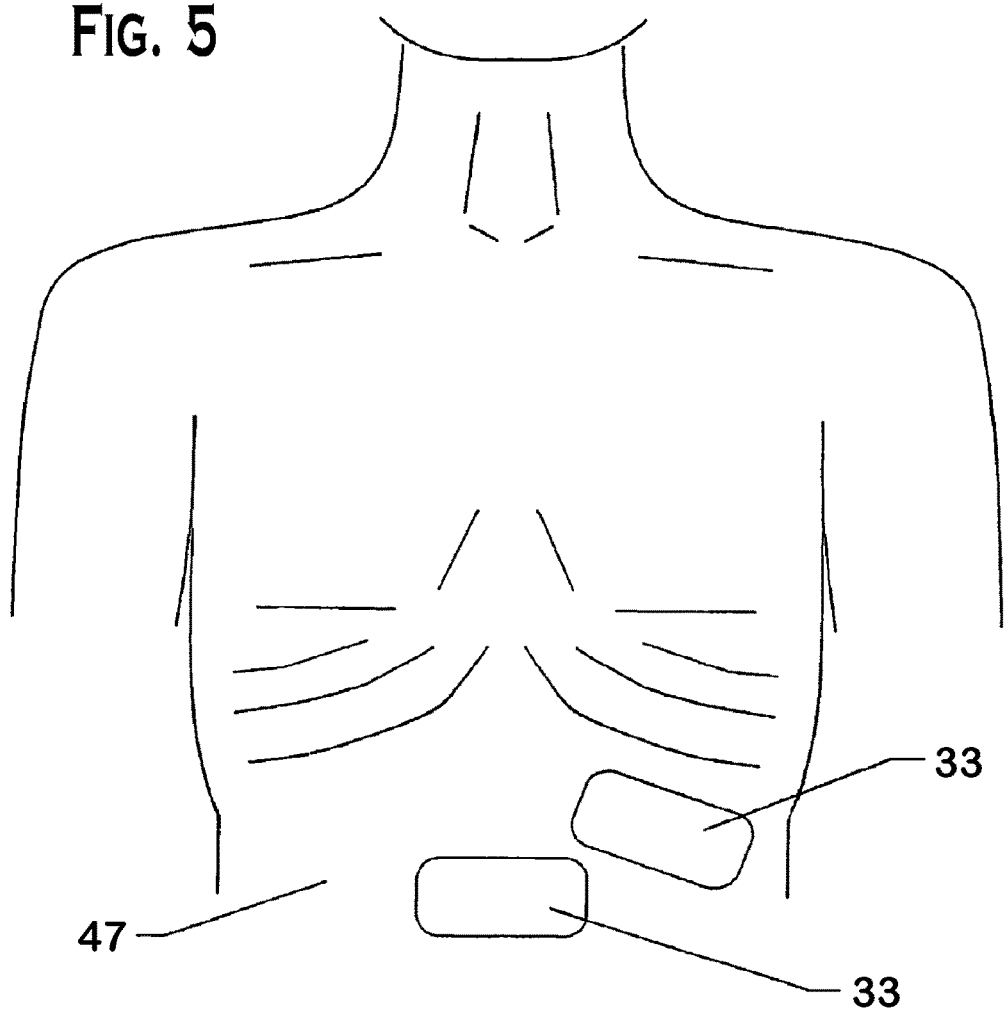
FIG. 5 is a drawing of the patch embodiment of the invention worn by its subject.
Figure 6:
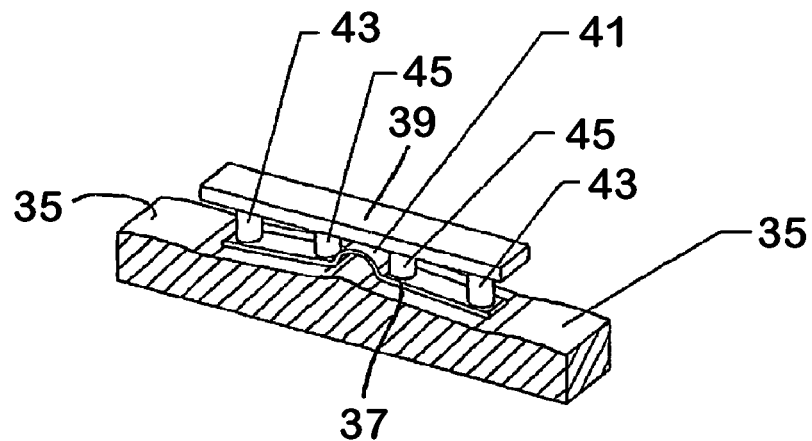
FIG. 6 is a drawing of a flex transducer for a bending sensor mode.
Figure 7:
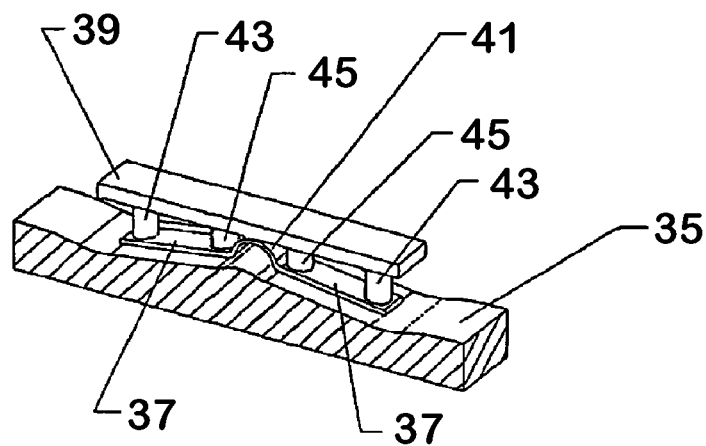
FIG. 7 is a drawing of a flex transducer for a bending sensor flexed downwards.
Figure 8:
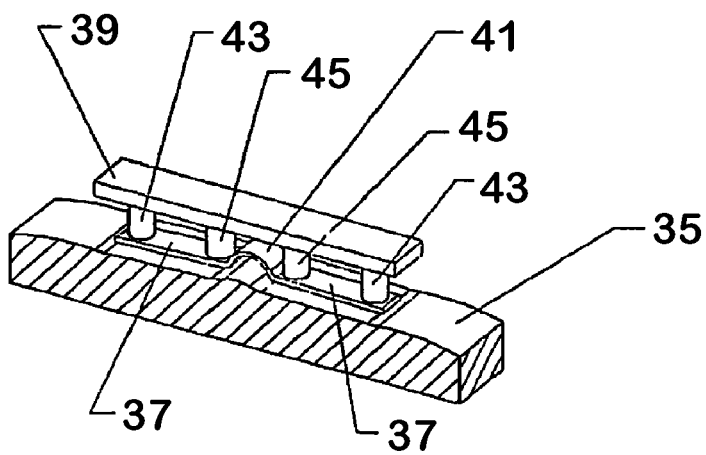
FIG. 8 is a drawing of a flex transducer for a bending sensor flexed upwards.
Figure 11:
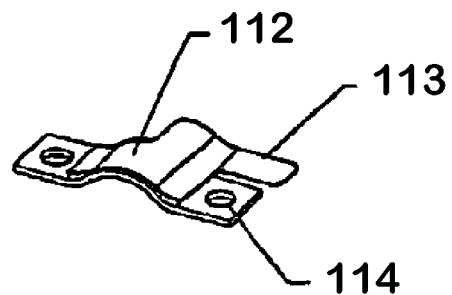
FIG. 11 is a drawing of a flex sensor and support.
Figure 12:
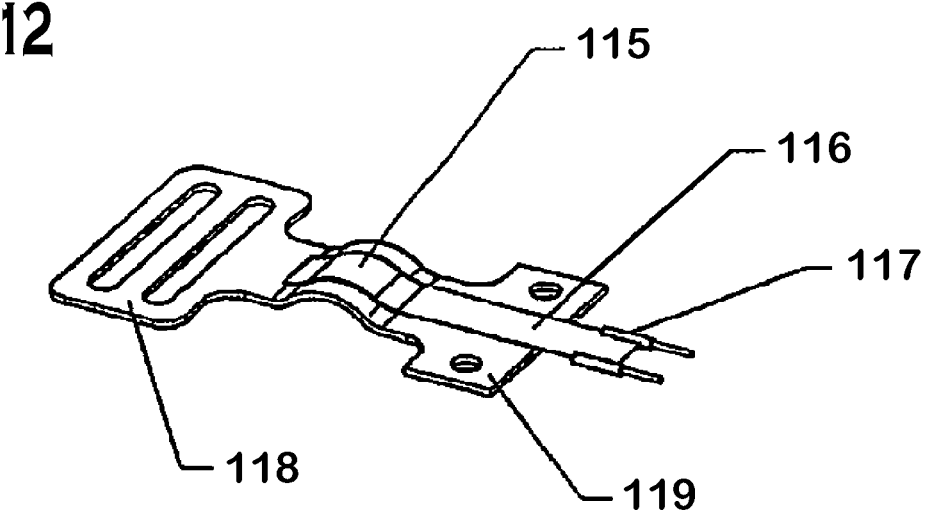
FIG. 12 is a drawing of another flex sensor and support.

In another configuration shown in FIG. 5, the transducer means is employed as a bending sensor that could be embodied in a patch 33. As shown in FIGS. 6-8, the transducer is attached between two projecting arms such that the rotation of either arm relative to the other will produce a change in electrical resistance. A flexible pad or backing 37 is applied to one side of this transducer assembly. A pressure applicator 39 is provided to compress the entire assembly against the subject's abdomen, oriented so that the flexible pad is placed flat against the skin. The pressure applicator may consist of a belt or strap, an external clamp or fixture, or an adhesive pad 33 that attaches to the surrounding skin. The pressure applicator is configured such that force is applied near the proximal and distal ends of each projecting arm with approximately equal force so that the flexible pad conforms to the curvature of the skin. The pressure applicator is further configured such that the mechanical compliance of the pressing elements is greater at the proximal ends than at the distal ends of the arms. When the subject inhales the abdominal wall expands. At the proximal ends of the arms the greater compliance acts to resist this motion to a lesser degree than at the distal ends. The result is a relative rotation of the two arms and a corresponding change in resistance of the transducer means. When the subject exhales the rotation is reversed, causing an opposite change in resistance.

Additional embodiments may be generated by employing multiple transducers and multiple straps, harnesses, or pressing devices. Further, the strap or pressing devices may be fabricated as, or incorporated into, a garment, and may support additional sensors or other devices. In either embodiment, the varying electrical resistance may be converted into a voltage or current signal using a variety of electrical circuits and may be converted to a digital or modulated format for additional processing.

FIGS. 6, 7, and 8 show schematically the alternate means of sensing respiration using a similar sensing element but without the need for a belt around the subject. In this configuration the sensing device is pressed against the abdomen of the subject. FIG. 6 shows the configuration at a neutral position. The skin and underlying tissue of the abdomen 35, shown in section view, are pressed against by two flat extensions 37 that are connected by an arched section 41 on which a resistive sensing element is mounted in the manner previously described. Similarly, a rotation upward or downward of one attached object relative to the other will cause a respective decrease or increase in flexure and thus a respective decrease or increase in resistance. A rigid or semi-rigid backing 39 is fixed at a short distance from the skin surface. Compliant elements 43, 45 fit between the backing and the flat extensions and act to press the flat extensions against the skin. The compliant elements may be springs, foam rubber, or any other springy material. The compliant elements 45 at the proximal ends of the extension have a different degree of compliance than the compliant elements 43 near distal ends, either using different material or different geometry. In this illustration the compliant elements at the distal ends may be considered to have the greater compliance or to be rigid. The abdominal wall can be considered as an elastic surface that will deform when pressed by the flat extensions. Not shown in the illustration is a pad or separator that would typically lie between the flat extension and the skin and which would act both to protect the electrical elements from moisture and to more smoothly distribute the force applied to the skin for better comfort.

FIG. 7 shows the effect on this configuration when the subject inhales. The abdominal wall expands, increasing the force against the flat extensions. Because the abdominal wall is elastic, the force will be distributed against the flat surface and balanced by deflection of the compliant elements. The more compliant elements 45 will deflect to a greater degree, causing a rotation of the flat extensions and increasing the flexure of the center section and thus the electrical resistance of the attached resistive element. FIG. 8 shows the opposite effect when the subject exhales and the abdominal wall contracts. The flat extensions rotate in the opposite direction, reducing the flexure of the center section and thus decreasing the electrical resistance.

The geometry and configuration of this type of sensing element can be varied in many ways. The required factors are the application of a force against the skin, a differential compliance such that a differential motion results from expansion and contraction of the abdomen, and a resistive sensing element placed so that its degree of flexure changes as a result of the differential motion.

FIG. 5 shows two preferred locations 33 for this type of respiration sensing configuration against the abdomen 47. The configuration may be placed to the side, directly below the ribcage or across the centerline of the body.

An electronic circuit is provided for analysis of signals affected by the flex sensors to determine respiration rate. The circuit simply looks for high and low peaks in the input signal and determines the peak to peak (p-p) time and amplitude. The results are compared to predefined min and max cycle times and a threshold amplitude to determine the presence or absence of breathing. The cycle period, p-p amplitude (arbitrary scale), and ratio of inhalation to exhalation times are reported. The analog input is digitally filtered to remove signals above 1 Hz. A second order filter would remove "movement" signals. A secondary circuit may be applied to "score" the output signal over a longer period, perhaps 60-180 seconds, and so produce a more reliable estimate of the presence of absence of breathing. This may take the form of "minimum of X seconds of breathing detected during the previous Y seconds."

In addition to detecting respiration rates, the electronic circuit associated with the flex sensor reports the presence of body motion as seen as signals above 1 Hz. After applying a 2nd-order high pass filter to the analog signal, the result is rectified (absolute value). The result is compared to a reference. If it is greater than the reference an output flag is switched on and a timer is (re)initialized. The output remains on until the timer runs out—typically in 0.1-0.5 seconds. The intent is that activities such as walking will cause the output to remain on continuously. Alternatively, the rectified signal may be processed with a 1st order low-pass filter with a >1 sec cutoff to generate an envelope signal. The envelope signal is compared to a predefined reference level and a yes/no output is generated. This could be expanded to report multiple levels, signal frequency, or peak values.

Motion Sensing

An accelerometer is included in the electronic circuit as the primary means for motion sensing and sensing the orientation of the subject (e.g. standing, lying down). However the flex sensor may be used by the electronic circuit to provide a backup signal for the accelerometer. A useful feature of the motion signal obtained from the respiration detector is that it is shows particular sensitivity to localized upper-body motions. This contrasts with the accelerometer, which is sensitive to any acceleration of the torso.

The electronic circuit may also include correlation of multiple sensor inputs, particularly of the respiration sensor and accelerometer. Alternately this can be provided in software. The primary intention is to provide improved confidence levels for the quality of processed signals. A simple example is that the apparent presence (or absence) of a detected respiration signal may be considered meaningless if a large accelerometer output in a similar frequency range is detected.

Sensor Electronics

The LSDS gathers certain physiological information and sends it first wirelessly to a local receiver or transceiver for retransmission to a separate computer station such as a PC or PDA. The unit measures heart rate by detecting and timing ECG R-waves, determines physical activity and orientation using an accelerometer, determines respiration rate by reading a chest expansion sensor, and measures temperature. These life signs are then analyzed using a health state determination algorithm. The resulting health indications, plus the raw data behind them, are transmitted out of the LSDS preferably every two seconds, or this period could be allowed to vary. Alternatively, if nothing has changed, energy could be saved by transmitting a "nothing changed" signal.

Major Component Overview

Figure 13:
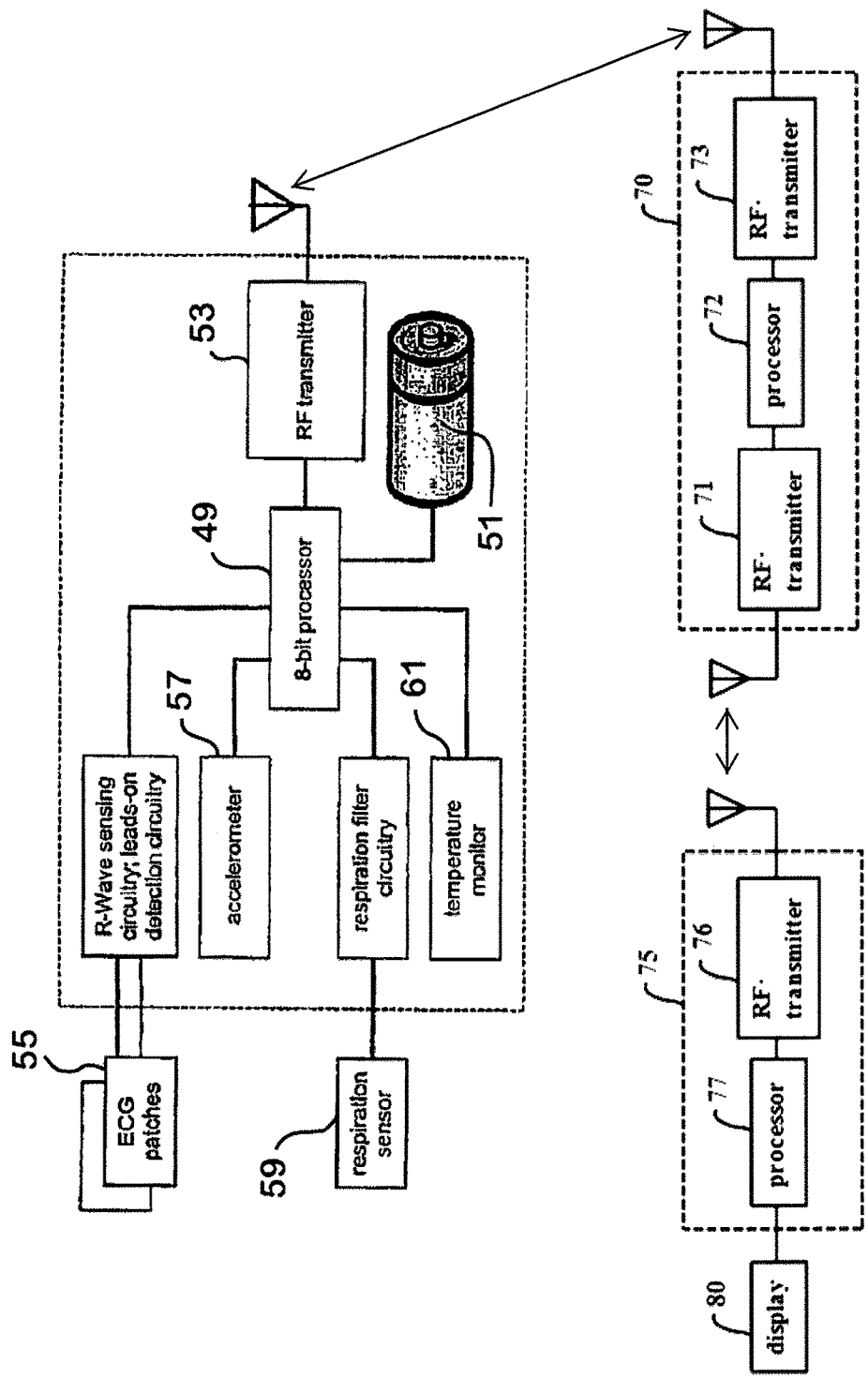
FIG. 13 is a block diagram of the electronics of the LSDS, local hub, and remote base station.
Figure 14:
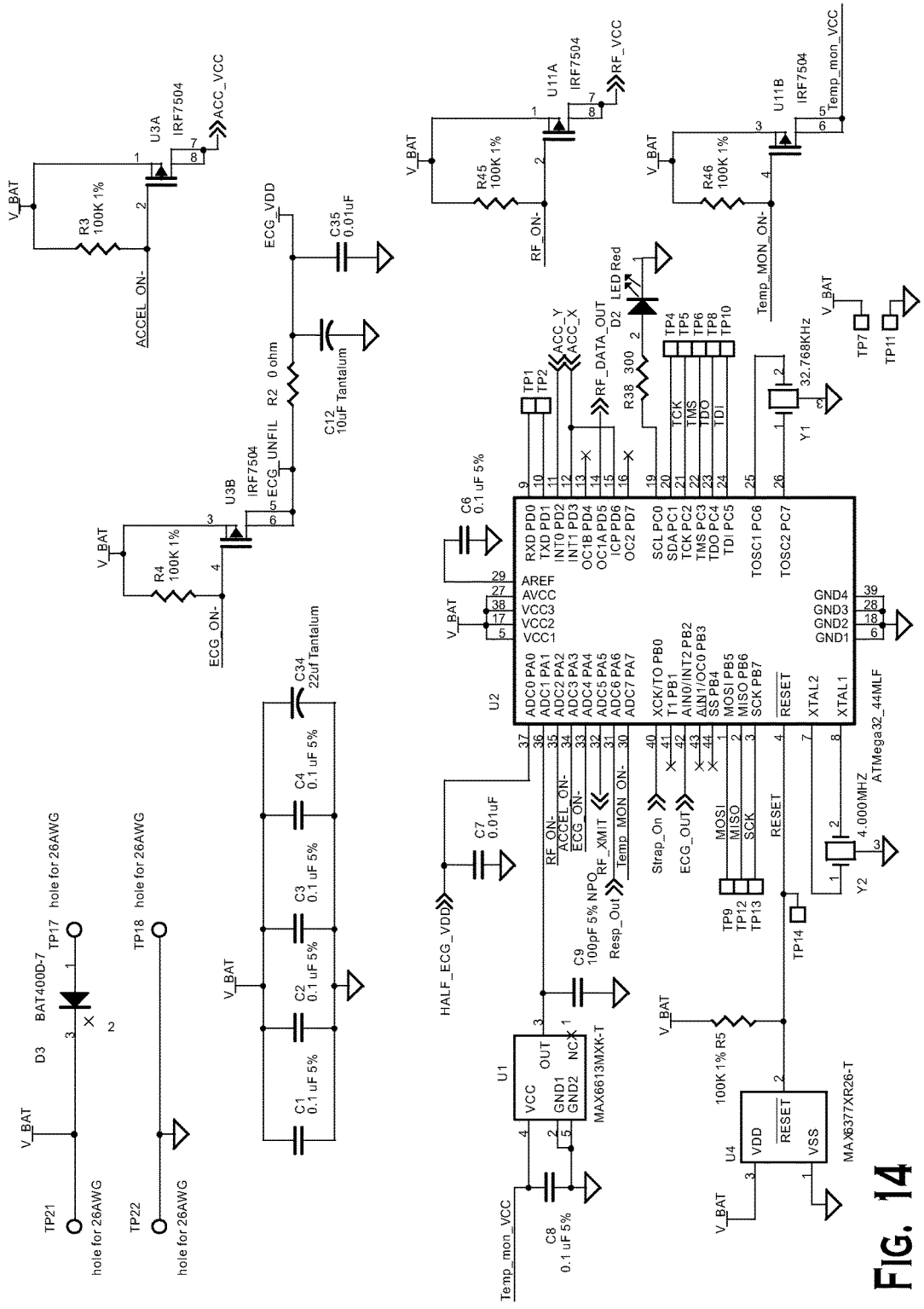
FIG. 14 is the circuit diagram for the on board processor and power control
Figure 15:
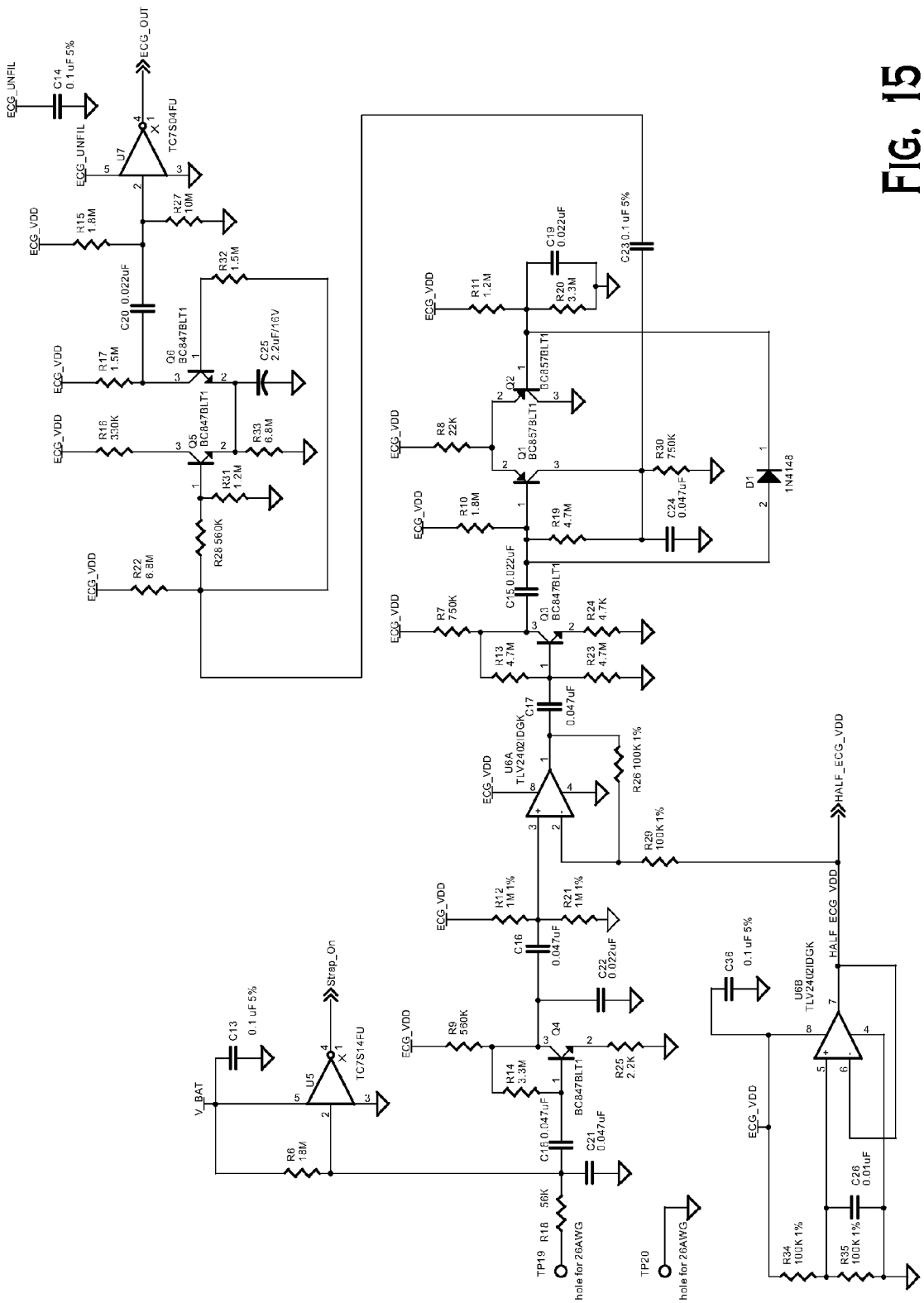
FIG. 15 is the circuit diagram for the ECG front end circuitry.
Figure 16:
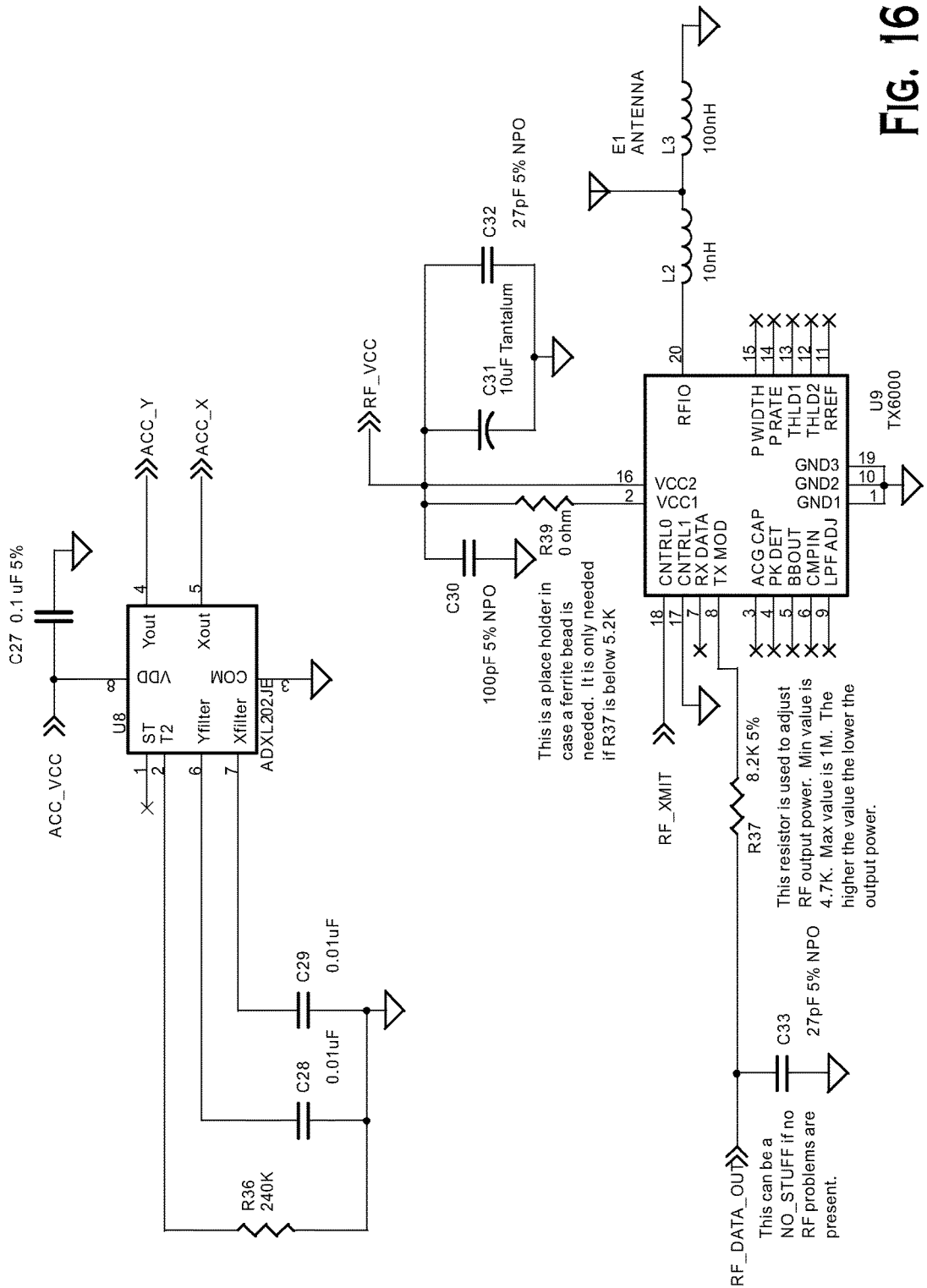
FIG. 16 is the circuit diagram for the accelerometer and RF circuit.
Figure 17:
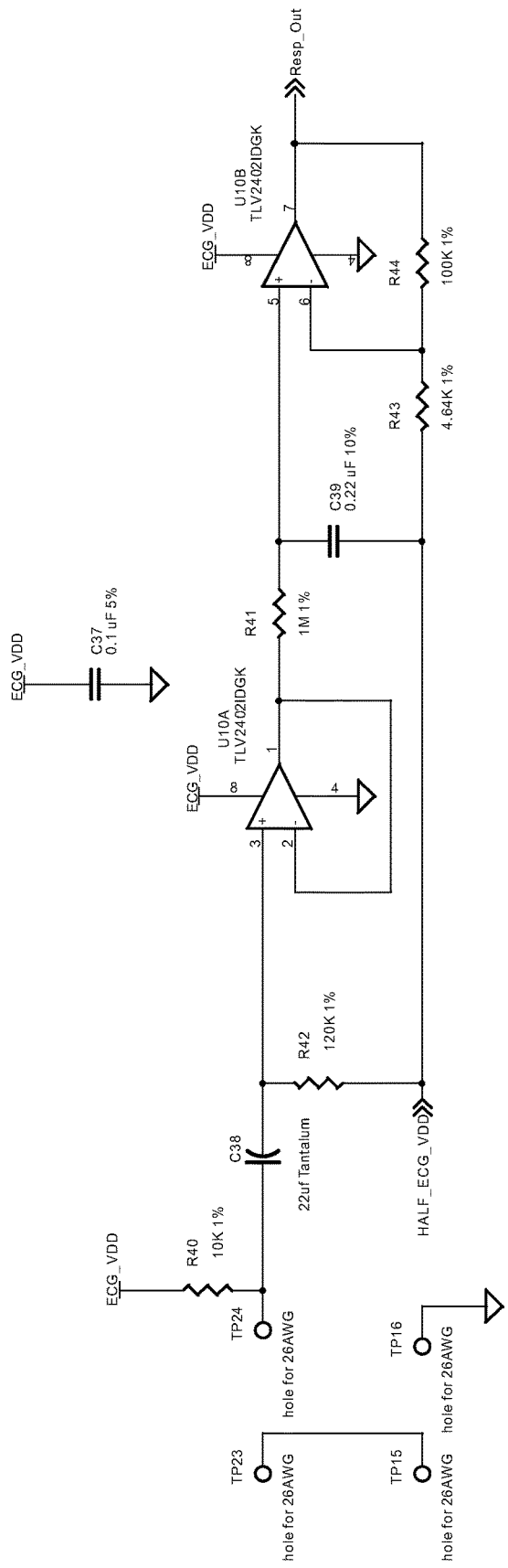
FIG. 17 is the circuit diagram for the respiration circuitry.

The sensor contains an 8-bit processor surrounded by various sensor inputs and an RF transmitter. A block diagram of the electronics is shown in FIG. 13. The full circuit diagrams are presented in FIG. 14 (Processor and Power Control), FIG. 15 (ECG Front End), FIG. 16 (Accelerometer and RF circuit), and FIG. 17 (Respiration Circuitry).

Referring to FIG. 13, a microprocessor 49 such as an Atmel AVR Mega32 processor is used. Typical requirements for the processor are low power draw, suitable program memory (16K words), suitable RAM memory (2K bytes), EEPROM for nonvolatile storage, general purpose I/O, analog inputs, external interrupts, versatile timers, high and low speed clocks (4 MHz and 32.768 kHz), flexible low-power sleep modes, in-circuit programmability; and easy to use development tools.

To conserve battery life, the processor makes extensive use of sleep modes. There are two crystals attached to the processor, one that runs at 4 MHz, and one running at 32.768 kHz. The high speed crystal keeps the processor when it is awake, and the lower-frequency crystal keeps the internal timers running when both awake and in the low-power standby mode.

A Lithium-Polymer (LiPoly) battery is used because of its high power density, various thin packaging options, and lack of memory effect (as is experienced with NiCad wo 2005/046433 PCT/US2004/036587 and NiMHd battery chemistries). The preferred battery used in the LSDS strap is rated at 560 mAHr.

The battery voltage is monitored by feeding ½ of the battery voltage into one of the processor's AID inputs. This ½ Vbat is also used by the ECG detection circuitry and is a convenient voltage for monitoring battery health. A fully charged battery is at about 4.2V, and the battery will operate normally all the way down to 3.2V, at which point the circuit will be shut down to avoid erroneous reports. Beyond 3.2V the voltage will drop fairly rapidly when under load.

The output of the sensor is intended to be transmitted to a local receiver (local hub 70) for further transmission to a more remote station 75. Local hub 70 contains a processor 73, a transceiver 71 that receives signals from the short range transmitter 53, and a transceiver 72 that transmits signals more remotely to the remote base station 75. Remote base station 75 includes a processor 77 and a transceiver 76 for receiving signals from local hub 70, and is connected to an external display 80. The RF Monolithic (RFM) TX6000 is a 916.5 MHz transmitter 53 that operates at 3V and draws <10 mA when on and draws virtually no current when in sleep mode (between transmissions). A 1 kHz Manchester-encoded data stream is sent out the RF transmitter once every two seconds. The transmitter uses simple on-off keying, thus only drawing power when transmitting a "1".

Transmit range depends on the length and shape of the antenna, the orientation of the antenna, and how close the antenna is to the body and the electronics in the LSDS strap. Maximum range is about 50 feet. Lesser range would consume less power, reduce interference with other devices and reduce detection by an adversary.

A pair of conductive rubber pads 55 picks up the ECG signal generated by the heart. A single-ended input circuit (one input is ground) amplifies and filters the ECG input. An adaptive comparator looks for the high slew rate of the R-wave component of an ECG pulse, allowing the circuitry to detect strong and fast heart rates as easily as weak and slow ones. The analog "front end" is a slew rate detector circuit with sensitivity down to 0.15 mV when no appreciable noise is present. This analog circuitry draws very little current, allowing it to remain continuously powered-up when the LSDS is on-body.

An ADXL202E two-axis accelerometer 57 is used to detect both activity level and orientation. This version of the device puts out a pulse-width-modulated pulse train that is timed by the processor. It is turned on by the firmware only when read, and left off at all other times. Only one axis, the one that corresponds to the vertical axis when the wearer is standing upright, is used. Thus the sensor can distinguish a standing subject from one lying down, but cannot tell on which side he/she is lying. The second accelerometer axis can easily be used, allowing side-to-side orientation sensing as well.

Respiration Sensor and Circuitry

Tension sensors 59 are built into each end of the LSDS plastic shell. These variable resistors change value as the chest expands and contracts. The LSDS circuitry changes this resistance into a voltage that is then frequency limited using a 0.25 to 2.5 Hz band pass filter. The resulting signal is then sampled by the processor using one of its built-in analog-to-digital inputs, while the rest of respiration sensing is handled in firmware.

The sensor has a nominal resistance of approximately 5K ohms. The resistance change at maximum load: approx. (−500) ohms. The required analog bandwidth is 0.06 Hz-4 Hz. The low pass (4 Hz) cut-off matches the available 8 Hz sampling rate. This should be adequate, although 6-8 Hz appears to be optimum. A 1st order filter may be adequate for the 4 Hz cut-off. The sensitivity of the sensor falls off at higher frequencies. Aliasing of signals up to 10 Hz will be correctly interpreted as body movement.

The high pass (0.06 Hz) cut-off has been chosen to match the slowest normal breathing rate. It is intended primarily to provide decoupling of the sensor's DC offset. When the sensor is to be used to sense heartbeat, an analog bandwidth of approx. 75-100 Hz is required. Because this would most likely be used as an occasional "last resort" measurement, it may not be preferred to provide analog wave-shape detection. The microprocessor could simple sample at a 150~200 Hz rate for a period of 5 to 10 seconds and process the signal to determine whether a heartbeat is present.

A Maxim MAX6613 temperature sensor 61 is used to measure the temperature of the circuit board. Since the plastic LSDS enclosure is pressed snugly against the skin, the temperature read by the sensor tracks the true skin temperature after a short thermal delay period. The sensor has better than one degree C. accuracy over a 5 C to 50 C range. The sensor converts temperature into a voltage in a very linear fashion, and this analog result is fed into one of the processor's A/D inputs. Since it draws so little power, it is left on when the strap is on-body.

Power Control

In order to extend battery life to its fullest potential, the ability to turn sections of the circuitry on and off is crucial. Power switching is under control of the processor. Some devices have power control inputs (e.g. the RF transmitter), while other devices are turned on and off using a high-side low resistance FET switch. Power to these devices is gated by the FET transistors whose gates are attached to processor outputs.

Power Management

Figure 18:
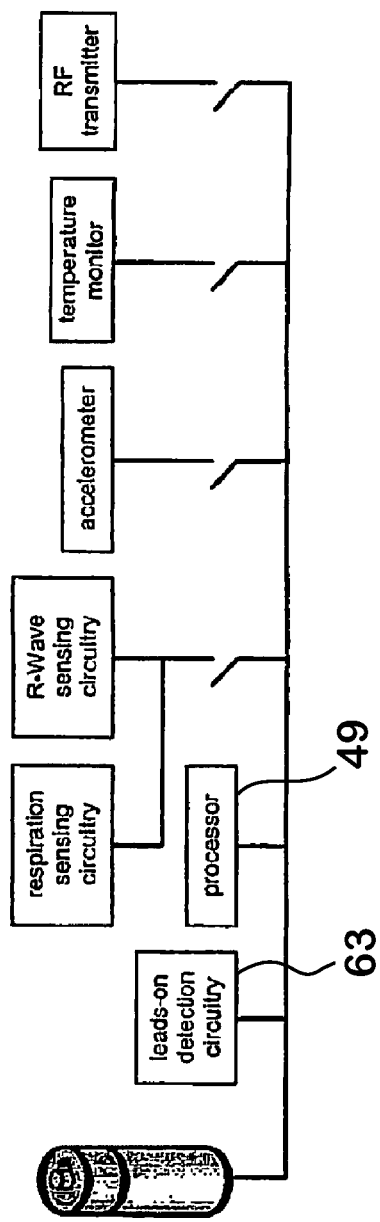
FIG. 18 is a schematic representation of the power management scheme.

A simple representation of this power management scheme is shown in FIG. 18. Some switches will be closed whenever the LSDS is on-body, and other switches are closed only when needed. The leads-on detection circuitry 63 is always attached to power since the processor always needs to know when the LSDS strap has been put on-body or taken off-body. Similarly, the processor is also always powered up, although it enters a low-power mode whenever possible.

Program Organization

Figure 19:
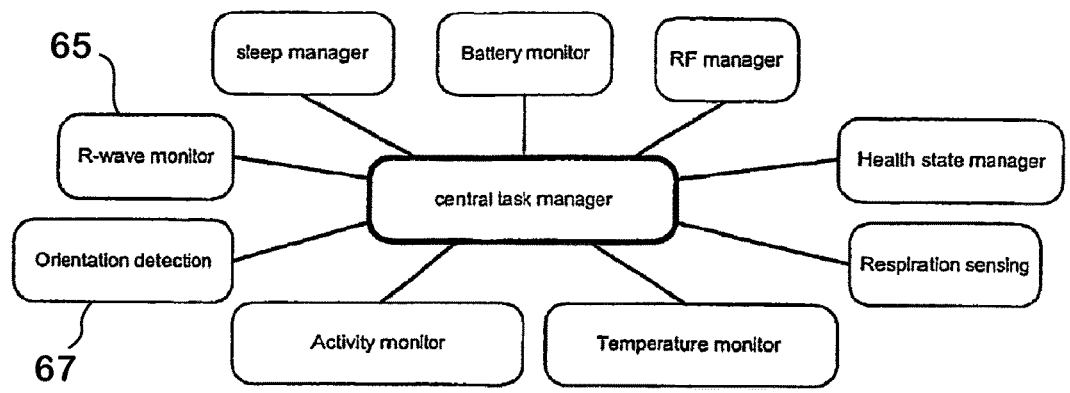
FIG. 19 is a block diagram of the major tasks of the central task manager.

The firmware program stored in the microprocessor is organized according to the major tasks that are to be performed. A task manager schedules the execution of each of the tasks. By having each task operate as a state machine, task switching can be done at a very fast rate, resulting in the illusion that all tasks are running simultaneously. FIG. 19 is a block diagram of the major tasks.

Each task has a different operating mode, depending on whether the strap is on- or off-body. In most cases nothing is done when the strap is off-body. When on-body is detected (and debounced) by the sleep manager tasks, all of the other tasks turn on certain circuitry (as needed), initialize certain variables, and begin to perform their respective functions.

R-Wave Monitoring

The heart rate algorithm receives an interrupt every time an ECG pulse is detected. Since EMG and electrical noise caused by skin stretching and ECG sensor contact motion all cause interrupts on the ECG input to the processor, the heart rate algorithm performs a good deal of filtering in order to isolate the desired R-wave pulses.

Orientation Monitoring

Orientation is determined by looking at the value of the accelerometer. Since the accelerometer is calibrated to detect gravity, a +1G acceleration means the unit is upright, 0G indicates horizontal orientation, and somewhere in-between means the strap is at an angle. Orientation is only measured when the activity level is between low and none.

Activity Monitoring

Activity is measured periodically in order to determine how much movement the user is experiencing. The accelerometer is turned on and sampled at a 4 Hz rate in order to reduce battery consumption. A sudden/short movement may be missed, but the next movement may be measured instead. This task simply looks for the highest amount of acceleration that is sampled, and holds this level for a few seconds, as a peak-hold circuit would operate.

Temperature Monitoring

Since temperature is not expected to be changing at a fast rate, temperature is only measured every 15 seconds in order to save battery power. This task has multiple states since the process includes reading an A/D input channel and then converting the result into a temperature.

Power control settings may be variable, e.g. so that at low battery the system might choose to collect and transmit fewer vital signs, provided that sufficient remain for the life assessment.

Respiration Monitoring

The respiration monitor task samples the bandwidth limited chest expansion voltage at an 8 Hz rate, and then performs a simple analysis to determine when breathing is occurring. The algorithm first determines when the wearer is inhaling or exhaling. This is done by looking at the relative change in the sampled signal, effectively taking a first order derivative that removes the DC component of the signal. Once a binary signal (inhaling or exhaling) is produced, it is timed and analyzed for consistent behavior. If several similar (+/−25%) timed breaths are seen, they are averaged together and used as the final respiration value. If no consistent breaths are seen in a 30 second period, the respiration rate is set to "unstable". If no chest expansion/contraction is seen for over a minute, respiration rate is set to zero.

Health State Manager

This task runs an algorithm (or algorithms) that determine the current health of the wearer based on all available physiological information. Recent historical physiological information is kept in an array and is used to determine both the health of the user and the confidence of the assessment of health. The resulting health state is not used on-board, but is instead simply transmitted as part of the RF packet. Alternatively, the assessment could be used locally to decide the rate at which to monitor events.

RF Manager

This task transmits data. Transmissions are preferably repeated every two seconds or at a variable rate. Whenever it is time to transmit a packet of data, the RF manager task simply gathers the most recent physiological information, calculates the appropriate checksum (or other error correcting codes), and builds a packet of information for transmission. In order to maintain tight timing on the Manchester-encoded data, a timer interrupt is used to shift out the actual data bits. In other words, once the packet has been built by the RF manager task, the tither interrupt takes over and shifts out all of the data with the appropriate timing.

Battery Monitoring

The battery monitor task periodically measures the battery voltage level in order to determine the health of the battery. Since batteries tend to have a "knee" at which the voltage drops off rapidly, only a "low" and "not yet low" determination can reasonably be made. Any voltage above 3.6V is interpreted as a healthy battery. About 95% of the time the battery will be above this "knee" voltage. When the voltage drops below 3.6V, the battery monitor interprets this as a "low" indication. When the battery drops below 3.2V, the battery monitor changes its indication to "dead", meaning that there is not much time left before the strap stops operating. The exact timing for each of these battery levels depends on strap use, how well the battery was charged, and how old the battery is. In general, a fully charged battery will operate over two weeks on-body before entering the "low" state, then operate another hour or more before entering the "dead" state. Even then, the unit should continue to operate with a "dead" battery for 10 minutes or more.

Sleep Manager

This task reduces battery consumption by putting the unit into a power-saving sleep mode as often as possible. The firmware puts the processor to sleep even when the strap is on-body. The difference in sleep mode use between on-body and off-body operating modes is that when on-body, the unit wakes up more often (8 times a second). The sleep manager looks at all of the states of all of the tasks when determining if the unit can go to sleep. If all of the tasks are in their respective "idle" states, and no action-pending flags are set, the firmware instructs the processor to shut down the main 4 MHz clock and wait for a timer or interrupt event to wake it up again. The unit spends almost all of its time in a low-current sleep mode, even when on-body.

Miscellaneous Functionality

There are three timers running in the background, two being at high speed and one being at a slower 8 Hz rate. None of the tasks described above run any more often than 8 times a second, allowing the processor to spend most of its time in sleep mode, when on-body. One high speed timer is free running and is used to measure short tithe intervals. The other timer is started and stopped as needed to provide additional timing resources.

Improved EMI Rejection

The Flex Sensor may act as antennae to pick up unwanted electro-magnetic noise. While the output signal may typically be filtered to remove this noise, it is usually preferable to minimize the initial noise pick-up. The standard Flex Sensor has one resistive and one conductive strip, joined at the end of the sensor opposite the contacts. Improved EMI rejection will result from a configuration with one resistive strip and two conductive strips. The conductive strips are placed on both sides of the resistive strip, and all three strips are joined at the end opposite the contacts—now three contacts instead of two. In connecting to a circuit, the two contacts to the conductive strips are connected to a fixed voltage level, typically either ground or supply voltage, while the contact to the resistive strip is used as the output. By these means the output portion of the sensor is completely surrounded by a portion that acts as an EMI shield.

Improved Moisture Resistance

The mode of operation of the Flex Sensor, in which micro-cracks open on the surface of the resistive coating, makes it inherently susceptible to moisture. Water and other liquids can flow into the micro-cracks, effective shorting these gaps in the conductor. In air, suspended water molecules and other suspended ionic particles may similarly enter the micro-cracks with similar results. A cover sheet with an adhesive backing may be used to protect the resistive element.

Reversed Bending

Two Flex Sensor elements may be printed back-to-back on a single substrate. If the substrate is bent in either direction, one of the elements will increase in resistance. The two sensors may be monitored independently. Alternately, the two sensors may be wired in series and connected between two fixed voltages, thus creating a voltage divider. The voltage output of the divider, measured at the junction between the two elements will increase when the device is bent in one direction and decrease when it is bent in the other direction.

The fabrication process may be modified to change the operating range. Immediately after the resistive ink is applied the substrate is bent into a concave shape; the ink is on the inside surface and so its length contracts relative to the substrate. The ink is allowed to dry, the substrate is straightened, and the material is processed to produce micro-cracks. Because of the contraction of the ink the cracks will be partially opened when the sensor is straight. The operating range of the sensor is shifted to provide a useful output signal with bending in both directions.

Transmission

Although to reduce bandwidth, processing is preferably accomplished on the LSDS, some processing may be left for the host (receiver). The LSDS processor transmits amplitude and duration values for respiration cycles but does not apply any threshold tests. The host (receiver) has the task of determining whether the amplitude and duration values fall within acceptable limits.

A running average of the amplitude and duration values of the last four respiration cycles is transmitted to the host processor, rather than the values for the current cycle alone. This provides a more consistent output, but may introduce a degree on indeterminacy.

A small hysteresis value is applied to the respiration signal to minimize false "end of cycle" readings due to noise in the signal. The hysteresis value is dynamically adjusted based on the amplitude of the previous cycle.

Communications Protocol Requirements

The communications protocols in use by this system must provide error detection or correction codes to ensure that the data is received as sent. The protocols used must provide the capability to be assigned to an upstream unit, so that a set of sensors may be assigned to a single hub, and a set of hubs may be assigned to a single remote station.

A local protocol provides the transport of data between one or more sensors and a single hub. Since there may be many sensors, the local data packet format is extensible, not requiring changes to the hub to accommodate new sensor additions.

Gaps in the sensor data must be accounted for, either by providing a filler packet (of perhaps just a timestamp), or by the indication that the sensor is no longer communicating.

A distant protocol provides the transport of data between a hub, and the remote station. This protocol must allow for interruptions in the data stream, with later recovery of data stored within the hub.

User Interface Requirements

The hub subsystem may provide a limited user interface in order to provide local health display (e.g. red/yellow/green LED's), and possibly a local selection mechanism to facilitate the initial association of one or more sensors to a specific hub. A more elaborate user interface is also possible if energy constraints are satisfied. The association of a specific hub to a remote station may be performed at the hub, or via the remote communications link, either to a medic PDA, or back to a remote station.

The remote subsystem has a more complex user interface to allow for the display of the basic status of multiple hubs within a single display, as well as being able to display additional status and data details from at least a single hub.

Medic PDA

The medic PDA subsystem has a user interface capable of displaying a list of hubs to connect to, and a mechanism to connect and display the detailed data as delivered by the hub.

Processing Requirements

The sensor subsystem is designed to: Capture and convert the analog data into digital form, perform error detection processing, to validate the proper application and operation of the hardware systems, battery status, etc., perform combined analysis of the biometric data, yielding the overall health metric, assemble and transmit the periodic data packets to the hub subsystem, and accept data received from the hub subsystem, applying configuration or command sets to update operational parameters.

The hub subsystem is designed to: Collect the periodic data from the sensor subsystem(s), buffering samples for transmission to the remote station; Provide minimal user interface capabilities to display the overall health status, and allow for sensor subsystem selection to be performed; Perform additional health status processing if multiple sensors are available to a single hub; Provide the uplink processing and data packaging for remote/PDA accesses.

The remote subsystem is designed to: Provide minimal status display of up to 20 hubs; Provide expanded status display of one selected hub; and Provide long-term data logging for all hubs connected.

The medic PDA subsystem is designed to: Establish a communications link to a single hub unit; and Provide display of all available sensor data and status information.

Communication Protocols

There are two communications protocols required as part of the complete LSDS design. The first protocol transfers data from the vital signs sensor to the hub, which in turn acts as a concentrator and relay to a remote station.

The Sensor-Hub protocol provides the communications locally between one or more body-worn sensors, and a physically proximate hub/gateway.

Packet Formats

General Packet Structure

In a preferred embodiment, every packet is required to provide the indication of the start of packet, which is done by encoding the packet length, followed by the ones complement of the packet length as the first two bytes. The packet length is defined as the number of bytes (octets) of the data payload, plus two so that the 16-bit CRC is included in the length. The packet data payload follows the header, and is able to be up to 253 bytes in length. The validation CRC follows the payload data, and is a standard CCITT polynomial CRC.

| Byte # | Description |
| --- | --- |
| 0 | Packet length (n) |
| 1 | Ones complement of packet length (~n) |
| 2 through n | Packet data payload |
| N + 1 | MS Byte of 16-bit CRC |
| N + 2 | LS Byte of 16-bit CRC |

Sensor to Hub Payload Format

There are two kinds of data transmitted from the sensor to the hub: sensor data and control data. Sensor data contains the data values obtained from one or more vital signs sensors that are present. Control data is sent in response to a command from the hub.

Sensor Data Packet Format

The format of a Sensor Data packet contains, at the minimum, the Sensor ID field, the first Data Present byte, and the health status field. If indicated in the data present field(s), other data will be present in the packet, in the order defined in the data present field.

Sensor ID 8 bits Assigned ID of Sensor

The Data Present is one or more bytes, with a bit set for each position that is encoded in the packet.

First Data Present byte

| Bit position | Description |
| --- | --- |
| 0 | Health Status |
| 1 | Heart Rate |
| 2 | Breath Rate |
| 3 | Motion |
| 4 | Vocalization |
| 5 | Temperature |
| 6 | Battery Status |
| 7 | Clear indicates end of data field bytes |

Second Data Present Byte

| Bit position | Description |
| --- | --- |
| 0 | Unused |
| 1 | Unused |
| 2 | Unused |
| 3 | Unused |
| 4 | Unused |
| 5 | Unused |
| 6 | Unused |
| 7 | Clear indicates end of data field bytes |

The health status field is the output of the overall health algorithm. This output will take the form of a three-state variable, followed by an integer confidence rate. The hemi rate field contains either the heart rate numeric value, in the range of 20-250 beats per minute, or an indication of a hardware- or software problem status. The breath rate field contains either the breath rate numeric value, in the range of 1-100 breaths per minute, or an indication of a hardware or software problem status. The motion field contains the indication of activity, as measured by an accelerometer, and will be in a 4-state range where lower value indicates less activity. A vocalization field contains data from the sensor. The temperature field contains the current body temperature in degrees Celsius. The battery status field contains a three-state (high, medium, low) value indicating the charge left in the battery. The sensor control packet is sent in response to a command from the hub. Its contents are dependent on the command that it is responding to. The Sensor ID contains the 32-bit unique ID for a sensor. This is used as part of the process of associating a sensor to a hub.

The data transmitted from the hub to the sensor contains command data only. These messages are for providing configuration values, and retrieving status information that is not periodically transmitted.

Sensor Commands

Attach Sensor: This command causes the sensor to become associated with the sending hub, and assigns an 8-bit sensor id to the sensor.

16-bit CRC generation and validation: CRC generation is preferable to a simple checksum due to the larger number of errors that a CRC will catch, that a checksum will not.

Error Handling

At a minimum, the CRC on each data packet will indicate the success or failure of data transmission. Any packet that fails the CRC check will be discarded, and will not be used in determining either the state of the system, or the health of the person it is attached to. If the underlying transport protocol does not support error correction measures such as retransmission, then a data packet that fails its CRC check will be discarded, and an indicator of this data loss inserted into the data stream.

Hub-Remote Protocol

The hub-remote protocol provides the information transfer between the hub, and a remote viewing station that may be either a medic PDA, or a grouped display.

Remote Display of Data

The software is divided into an upper and lower end, based at the point in which a valid packet has been received. In the case of a live connection, this is checked for in the timer loop once every 100 msecs, polling for new data received by the serial interface and collecting it into a packet. In the case of a replay file, a two-second timer is used to read in the next packet 'received'.

A valid packet, whether from a file or from the serial interface, is passed to the main message loop of the application. When this is received, the packet is parsed, updating the corresponding displays with the newly received data. In addition, the data received is formatted into an ASCII string in hexadecimal format, and displayed in the LSDS communications field. Live connections additionally count the number of packets that contained header errors or checksum errors and update their respective fields.

If the health status algorithm is enabled, it will be sent copies of the newly received data, which are placed into individual parameter data buffers for the next analysis phase. Preferably, once per second, the health status algorithm is executed on the data buffers, updating the display of the health status, along with the confidence score of that determination.

Configuration Dialog

The configuration dialog contains the controls to select between data input from a live sensor, and replay data from a log file, serial port setting controls for both the LSDS sensor, and the optional Propaq interface, and enable checkboxes for running a session with a Propaq collecting data, as well as enabling or disabling the local health status algorithm for processing on received data. It is preferred that when using the local health status algorithm, that a single ID be filtered for, as conflicting data from multiple sensors will invalidate the operation of the health status algorithm.

Main Dialog

The main dialog is where all of the relevant information from data collection and processing are displayed. The dialog is broken up into groups of related data:

LSDS Communications display provides a view of the communications from the LSDS sensor. As valid packets are received, the payload portion is displayed in ASCII hexadecimal notation within a scrolling text box. If header or checksum errors are detected, then the corresponding error counts are incremented.

Health Status displays contains the processed data from the LSDS sensor. It also contains the display of the Health State and confidence score both from the LSDS sensor, as well as the local implementation of the algorithm.

The set of icons and the states they represent are as follows:

BLACK health state: this means that no data has been received for 16 seconds

BLUE health state: this means that a valid determination is unable to be processed from the current data.

RED health state: this means that the health state is in critical condition, or possibly dead.

Yellow health state: this means that the health state is abnormal.

Green health state: this means that the health state is normal.

Red exception health state: this means that one of the red exception states has occurred.

The Propaq comms display provides a single status line indicating the operational mode of the Propaq communications interface, display of the received HR and RR values from the Propaq, and the difference, if any, between those values and the values determined by the LSDS sensor.

Every time the application is run, the data delivered as valid packets is copied out to the text replay file. This occurs after the id filtering is applied, and will therefore correspond to the data trace of a single LSDS sensor unit if filtering is active. The format of the data is in human-readable ASCII hexadecimal notation, one line per packet. The format of the packet is documented in the RF protocol document.

LSDS Packet Reception and Validation

The incoming data is received and buffered by the system serial device driver. Once every 100 milliseconds, any incoming data is collected and scanned for the expected start of packet sequence as documented in the RF protocol document. Extraneous data bytes are discarded after being logged in the binary packet file. Once a valid start of packet sequence has been detected, a counter is incremented for each new data byte, until the expected number of bytes have been received. Once a complete packet has been collected, then the checksum algorithm sums the data values, and compares it to the expected checksum field. If it is equal, then the packet is sent on for processing as a valid packet, otherwise, the data is ignored, and a new start sequence is searched for.

LSDS Data Field Processing

Each packet that has been validated contains essentially a snapshot of the LSDS sensor state. This data is validated against the expected range of values before being displayed, and if it is out of range, a display of ERR is used to indicate this. Additionally, if the alternate health status algorithm is active, then the data is sent to it to be used for evaluating the next health status result.

The ID data field is used only if sensor ID filtering is active. If the ID matches the filter ID, then the rest of the packet is processed, otherwise it is simply discarded. The Heartrate data field is used to display the current heartrate in the main dialog, as well as being subtracted from the most recent Propaq HR value to generate the delta HR field, if the Propaq interface is actively collecting data from a Propaq monitor. The Respiration data field is used to display the current respiration rate in the main dialog, as well as being subtracted from the most recent Propaq RR value, to generate the delta RR field, if the Propaq interface is actively collecting data from a Propaq monitor. The temperature data field is used to display the current skin temperature in the main dialog. The acceleration data field is used to select the appropriate label in the acceleration display in the main dialog. The orientation data field is used to select the appropriate label in the Orientation display in the main dialog. The Health status data field is the Health State as determined by the sensors' internal health state algorithm. It is used to determine the display in the Sensor Health State display on the main dialog. Confidence score data is the confidence score calculated by the sensors' internal health state algorithm. It is used to update the display in the Sensor Confidence field in the main dialog.

Health Algorithm Implementation

The design of the health status algorithm contains five processing steps: Data Gathering and buffering; Data summation (e.g. averaging) and conversion from numeric/symbolic into qualified range data; Rule lookup processing; Confidence scoring; and Result display. Of these steps, the first one is done asynchronously because of the nature of the communications medium, and is driven by the reception of data packets from the LSDS sensor. A one-second timer drives the rest of the processing steps, with all steps running to completion and generating a new health status and confidence score.

Data Gathering and Buffering

Each parameter has a 16-deep FIFO ring buffer for the collection of data from the sensor. Each sample in this buffer has, in addition to the value field, two flags, one to indicate that data was received, and one to indicate whether or not the data is valid.

The current sample index of these buffers is incremented once per second, whether or not data is received. As the current write index is incremented, the new sample index flags are cleared to indicate that no data is present. As LSDS sensor data is received, it is copied into the current sample index in the ring buffer. A minimal amount of processing is performed, only to determine if the data value is within the defined valid range of the sensor.

Conversion from Source Data to Qualified Data

Each parameter ring buffer is processed to provide the average value of the data within the ring buffer. For numeric parameters (HR, RR and Temperature), this is simply the arithmetic average (sum of the valid data values divided by the number of valid samples). For symbolic parameters (Acceleration and Orientation), this is done by counting the number of each enumerated value, and returning the one that has the greatest count. In the case of equal results, the enumeration with the lowest value is returned. This average value is then compared to the defined range boundaries, and the qualified data range value is returned.

Rules and Rule Processing

A rule contains a bitmap of qualified data range results for each parameter, along with a result state to be used when a match is found. Each parameter field in a rule will contain at least one of the defined qualified data results, and may contain the composite result masks. Once the current states of the ring buffers has been obtained, these states are compared to each rule until either a match is detected, in which case the corresponding health state is used, or all rules have been checked, in which case the default state of BLUE (unable to proceed) is used.

Confidence Scoring

The confidence scoring is performed last, since one of the input parameters is the determination of whether or not the current Health State has changed.

Once the health state and confidence score have been determined, then the new values are displayed on the main dialog, in the Hub Health State and Hub Confidence fields.

Heart Rate Calculation Algorithm

The algorithm works by tracking trends. A trend is defined as a somewhat consistent series of ECG pulses based on their timing. Several times a second a decision is made to keep using an existing trend or to shift to using a new trend. This means that several processes must be running in parallel, one that tries to track an already established trend, one that continuously looks for a new trend, and one that determines which of these two has better data, Incoming ECG information is filtered before presenting it to the trend tracking routines in order to avoid spending time working on noise pulses. ECG data is averaged and filtered, and then converted into an actual beats-per-second value.

Figure 20:
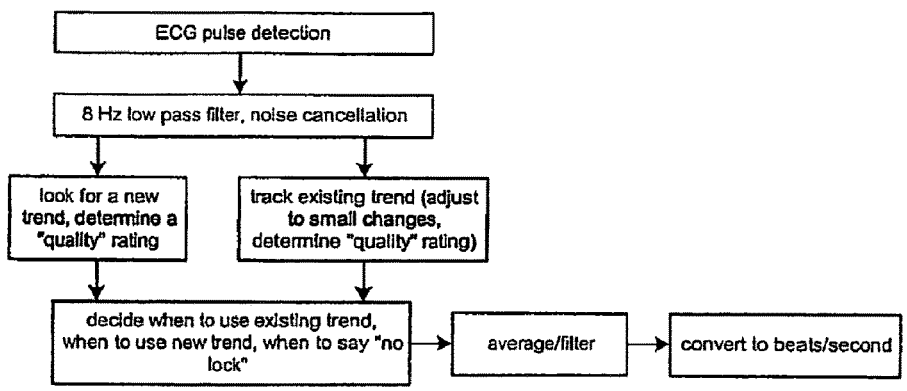
FIG. 20 is a block diagram of the Heart Rate Calculation algorithm.

A block diagram of this algorithm is shown in FIG. 20. Since each incoming ECG pulse is time stamped, those remaining after filtering and noise cancellation can be processed in non-real-time. This is useful since past or future pulse information is sometimes required to get a better understanding of the trend being followed and to allow for more tolerance of missing or extra pulses.

Timing

The slower the timebase, the easier it is to run the algorithm on a simple, 8-bit processor. Additionally, a timebase that uses a lower resolution clock allows the timebase to run while the processor is sleeping, reducing the drain on battery power. However, a more course timer resolution increases error (reduces accuracy) and makes it more difficult to implement simple per-beat timing comparisons.

A reasonable compromise is to use a 32 Hz clock as the basic timer. This allows per-beat intervals to be timed accurately enough to determine if a trend is present, shifted, or lost. Although a 32 Hz clock is not nearly fast enough to accurately time hemi rate on a per-beat basis, the averaging/filtering scheme described below looks at 4 seconds or more of ECG data. With a window of 4 seconds, a 32 Hz clock allows for better than 0.8% accuracy. A 32 Hz timer allows for an 8-second duration when stored as a simple 8-bit entity. This is plenty long enough for all pulse timing and averaging activities.

Process Timing

In order to keep processing power to a reasonable level and to allow the use of a small, inexpensive, and battery conscious microprocessor, processes are set up to run only at certain specific intervals, and this process repeat pace is kept to a fairly slow rate of once every eight seconds.

Figure 21:
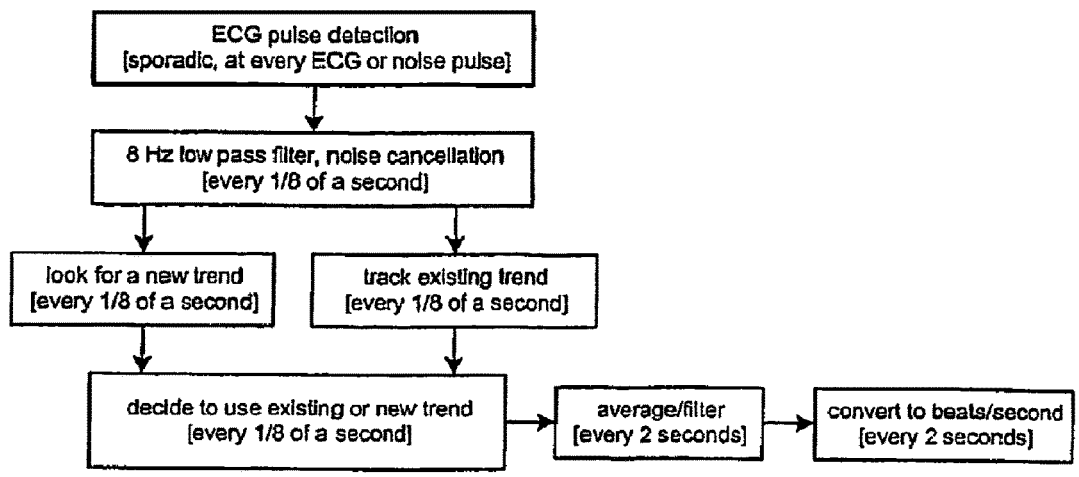
FIG. 21 is a block diagram of the process timing.

FIG. 21 shows how often each process is run. ECG pulse detection is performed whenever an ECG (or EMG or other unwanted signal) is seen, so its timing is sporadic and asynchronous to the rest of the process timing. The heart of the algorithm, which includes filtering trend tracking and analysis, is executed at an 8 Hz rate. Averaging/filtering is run only once every two seconds, and the resulting ECG rate is converted to a beats-per-second value every two seconds as well.

Algorithm Specifics

Figure 22:
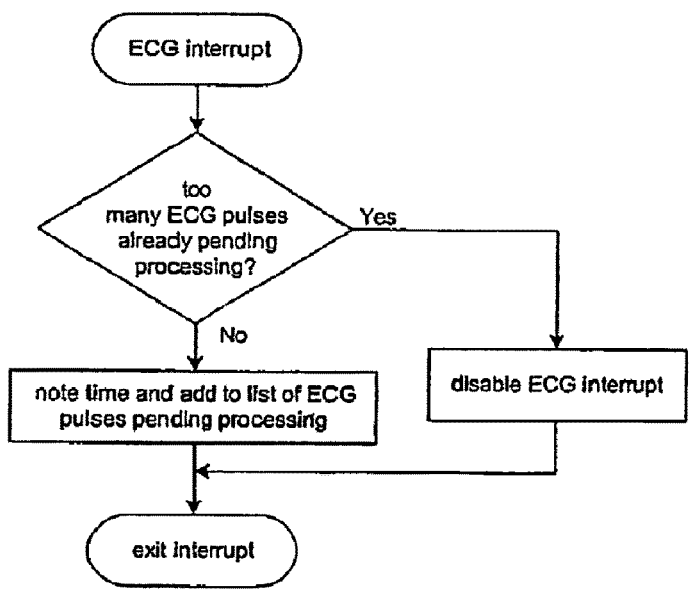
FIG. 22 is a flow chart of the ECG pulse detection interrupt circuit.

ECG, EMG and any other electrical impulse of sufficient magnitude cause an interrupt to the processor. The ECG pulse detection routine simply timestamps every interrupt and saves a record of its having happened. This information is used by the filter process. A flowchart of the ECG pulse detection interrupt is shown in FIG. 22. Since an incoming noise stream should not be allowed to flood the filtering process, the ECG pulse detection routine stops recording interrupts if too many ECG pulses are still waiting processing by the filtering process. The list of pending interrupts is cleared by the filtering routine on a periodic basis.

Low Pass Filter and Noise Cancellation

This process removes presumably incorrect ECG information by applying low pass filtering and noise cancellation. A low pass filter does not allow ECG pulses to come in too close in time to previous pulses, whereas noise cancellation simply deletes what appear to be extra pulses.

Figure 23:
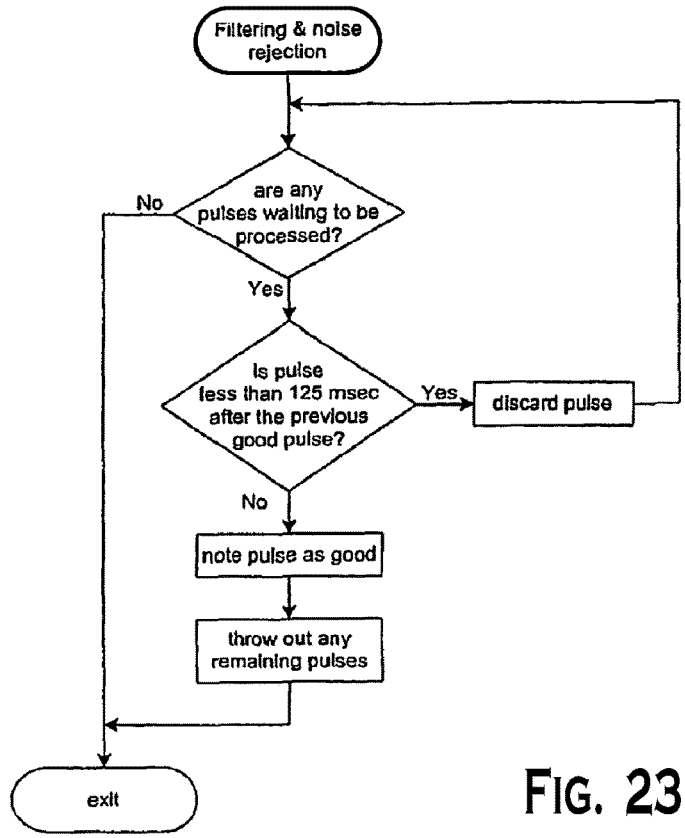
FIG. 23 is a flow chart of the low pass filter and noise cancellation circuit.
Figure 24:
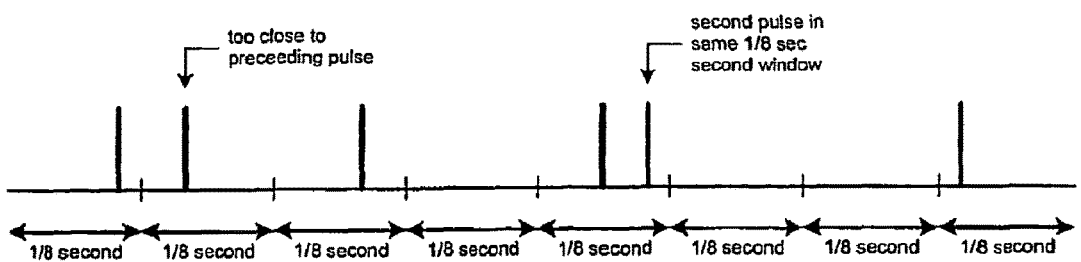
FIG. 24 is an example of pulses filtered for R-waves.

The low pass filter cutoff frequency is set to 8 Hz, which corresponds to a two-times sampling rate of 240 BPM. The filter works by throwing out incoming pulses that occur too close to the previous pulse. Since the filtering routine is run at an 8 Hz rate, the routine allows only one ECG pulse per ⅛ second period. If more than one ECG pulse is pending processing, only one is taken and the rest are ignored. A good example of when this filter is necessary is when there are echo ECG pulses due to both R and P wave detection. A flowchart of this filter is shown in FIG. 23.

Note that since this algorithm looks ⅛ second backward in time, a ⅛ second delay is introduced by this scheme. Once the ECG pulses have been processed, pulses seen in the previous ⅛ second window are passed on to the trend discovery and trend tracking stages of the algorithm.

Figure 25:
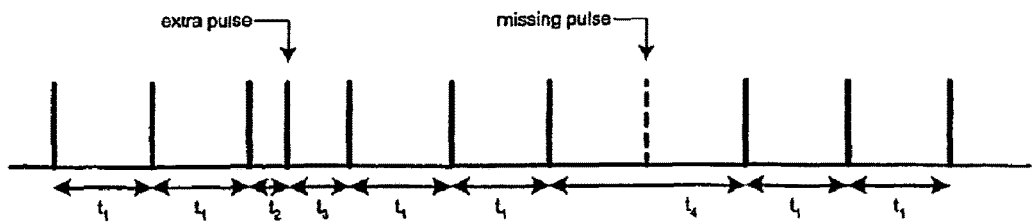
FIG. 25 is an example of pulses analyzed for consistent inter-beat intervals.

As an example of how this filtering scheme works, refer to FIG. 25. The first labeled pulse is ignored since it occurs too close to the proceeding pulse. The second labeled pulse is ignored since it is an additional pulse within the same ⅛ second time window.

Look for a New Trend

New trends are recognized by looking at only the most recent ECG pulse timing. A trend is defined as somewhat consistent timing of ECG pulses. Since noise can be expected and ECG pulses may occasionally be missed, the trend acquisition algorithm needs to be tolerant of extra and missing pulses. This is accomplished by looking at intra-beat timing and deciding which timing appears most often. As long as extra or missing pulses do not appear more often than true ECG pulses, this process should be able to find the correct heart rate;

The algorithm works by looking at four most recent inter-beat intervals and developing a scoring based on the consistency of these intervals. Since inter-beat intervals are not going to be exactly the same, a +/−12.5% window is allowed. With this size window, a missing beat will clearly be detected, and although an extra beat may appear inside this window, the following correct beat will appear later in time much less than the window size.

By looking at only the last four inter-beat intervals, the effect is that of a sliding window, leaving older information behind quite soon. This allows the algorithm to lock onto new trends fairly quickly, and also allows it to track slightly changing heart rates. Each new ECG pulse or perceived missing ECG pulse causes an update in the "score: for how well a trend is being seen. The rules for scoring are as follows:

if 3 in a row have similar timing, score=high
   if 3 of last 4 have similar timing, score=med. high
   if 2 of last 3 have similar timing, score=medium
   if 2 of last 4 have similar timing, score=low Using FIG. 25 as an example, inter-beat intervals are tracked as they occur, left to right. Interval $t_1$ is the normal heart rate, and it appears the most. When the extra pulse occurs, it creates the two shorter inter-beat intervals $t_2$ and $t_3$. Then, when a later pulse is missed; the longer inter-beat interval $t_4$ is seen.

In order to keep extra or missing pulses from adversely affecting the heart rate being calculated by the averaging process, only the consistent inter-beat intervals are saved in the history array. Again referring to FIG. 25, since $t_1$ is seen the most, only it will be saved in the history array.

Figure 26:
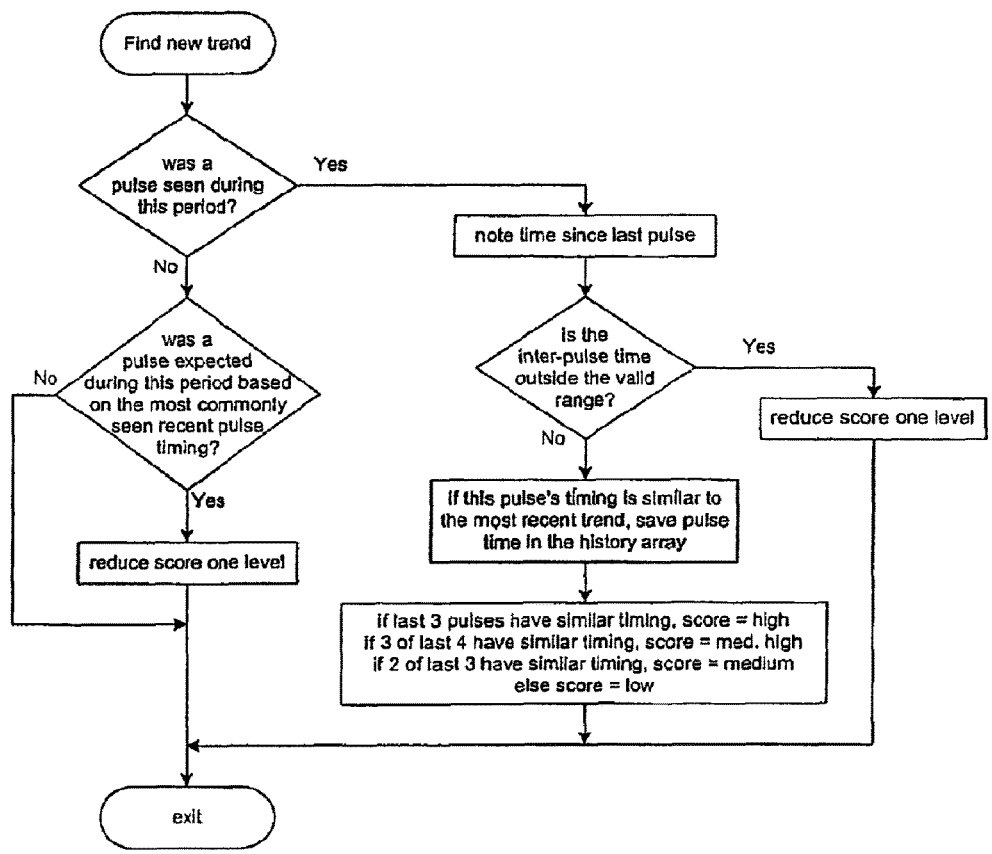
FIG. 26 is a flow chart of the trend-acquiring process.

A flowchart of this trend-acquiring process is presented in FIG. 26.

Tracking an Existing Trend

Figure 27:
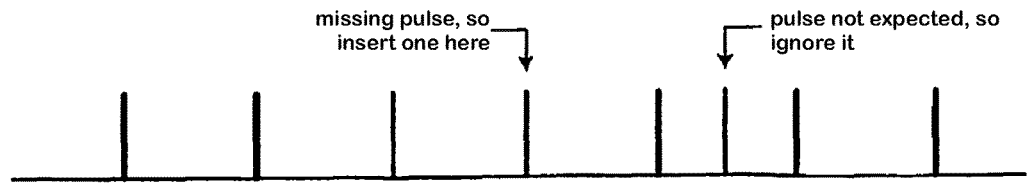
FIG. 27 is a diagram of R-wave pulses found when tracking an existing trend.

An existing trend is tracked by assuming the heart rate to be at a certain frequency, and then looking for more heartbeats at these expected intervals. Extra pulses are ignored in order to keep locked onto an existing trend in the presence of noise (extra pulses). Likewise, missing pulses are accommodated by assuming pulses to come at a certain time, and to allow for missing pulses as long as they sooner or later start showing up at the expected time. These actions are illustrated in FIG. 27.

In order to keep locked onto a slowly changing heart rate, a 12.5% window (+/−6.25%) of tolerance is allowed on each expected pulse. This size is selected since it is easy to calculate in integer math. With a tolerance window this wide, the hemi rate can change at a reasonable rate while still allowing this process to remain locked onto the moving trend.

Since extra pulses are ignored and missing pulses are assumed present, a near or perfect harmonic shift in heart rate will not be noticed by this process. For example, a jump from 60 to 120 BPM will not be noticed since at 120 BPM, a pulse is seen at the same timing as when the heart rate was 60 BPM, and the extra pulse in the middle is simply ignored. This indifference to harmonic shift is acceptable since a "look for a new trend" process will identify the proper heart rate of 120 BPM, and its score will be higher than that generated by this process.

Also, there needs to be a mechanism by which this "existing trend" process is locked onto a new trend when that new trend is seen to be strong and stable. The mechanism works by unlocking the existing trend when its score is low, and then locking onto a new trend when the new trend is seen to exist. This is how a harmonic shift is ultimately resolved, forcing the existing trend to lock onto the new, correct trend.

A score is maintained for how well the trend is being tracked. The rules for scoring are as follows:

if 4 of the last 4 expected pulses were seen, score=high
   if 3 of the last 4 expected pulses were seen, score=med. high
   if 2 of the last 4 expected pulses seen, score=medium
   if 1 or 0 of the last 4 expected pulses seen, score=low An array of inter-beat intervals is maintained in order to provide the averaging process the information it needs. In order to keep missing or extra pulses from skewing the averaging process, extra pulses are not recorded in the history array, and missing pulses are assumed present and are inserted into the history array.

Figure 28:
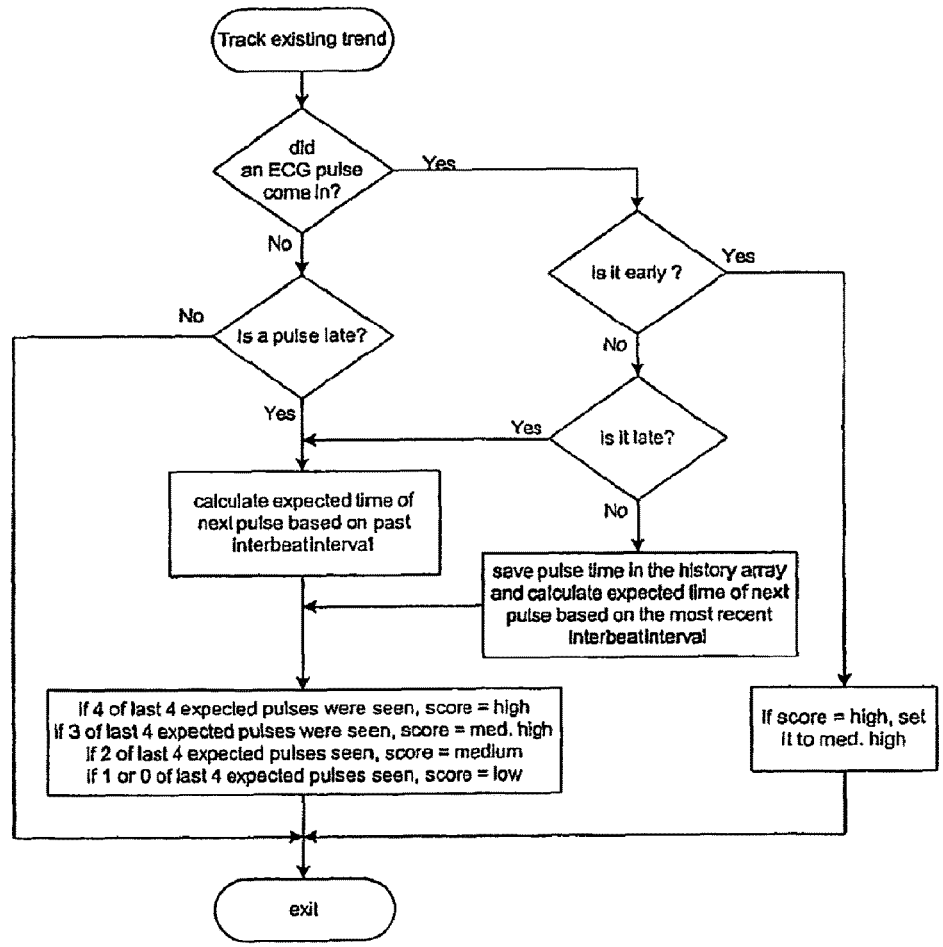
FIG. 28 is a flow chart of the trend-tracking process

The algorithm is simplified by recognizing the fact a maximum of one pulse can be seen or expected every time this process is run (8 times a second). A flowchart of this trend-tracking process is shown in FIG. 28.

Decide which Trend to Use (if any)

This process decides which set of inter-beat periods to use when calculating the heart rate. The scores generated by the "look for a new trend" and "track existing trend" processes indicate which array of historic inter-beat values are of higher quality, so the scores alone are the mechanism for making this decision. If both scores are the same, the historic data for the existing trend is used since it has a tighter tolerance on how much an inter-beat interval can change from beat to beat.

Since a good score will not always be available from either or both trend analysis processes, this process has two additional modes of operation. First, if both the trend the trend tracking and acquisition processes have low scores, the heart rate status is set to "unstable". Second, if there are no heartbeats but the ECG contacts are determined to be on-body, then the heart rate status is set to "none".

If neither trend contains useful information, this trend selection process makes two key decisions. First, if there have not been any heart beats in a while, the heart rate is set to zero. A timer is managed in the "low pass filter and noise cancellation" process that is cleared when an ECG pulse is detected and incremented when no pulse is seen.

Since that process is run every 1/8 second, the "no pulse" timer therefore counts at an 8 Hz rate. If the count exceeds a certain threshold, the pulse rate is set to zero and the rest of the trend selection process is skipped. Second, if either of the trend tracking processes has a low score and it is indicating missing pulses, the heart rate is set to a "slow heart rate" status.

Averaging Tilter

The averaging filter works by looking at the previous 4 to 6 seconds of inter-beat timing intervals. Faster heart rates will therefore be averaged over a larger number of heats than slower rates, but even at a low-end 30 BPM heart rate, three pulses can averaged in a 6-second window.

The algorithm simply looks back in time through an array of historic inter-beat intervals until it sees at least 4 seconds of pulse timing, and then averages this most recent pulse timing. The filter is run once every two seconds, so updated averaged hear rates are available every two seconds. Since only the most recent "good" inter-beat intervals are used in the formula, missed pulses will not have an impact on the algorithms ability to generate new averages every 2 seconds.

The coarseness of the 32 Hz timebase does not compromise accuracy as long as inter-beat intervals extend over a 4 second period of time. Each of the inter-beat intervals in the historic array of values taken alone is not very accurate, but when added together, their round-off inaccuracies cancel out.

Figure 29:
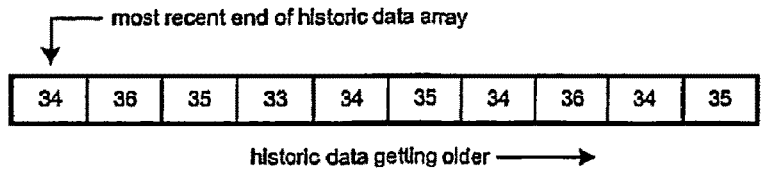
FIG. 29 is a chart showing the sample averaging scenario.

A sample averaging scenario is shown in FIG. 29. The heart rate is about 55 BPM, which corresponds to an inter-beat interval of about 35 counts (since the timer is miming at 32 Hz). The most recent inter-beat interval is seen to be 34. Moving back far enough to get at least 4 seconds of heart beats (4×32=128 total counts) takes one back to an inter-beat interval of 33. The average counts is therefore (34+36+35+33)/4=34.5 counts.

A final low pass filter stage is added that limits how fast the heart rate can change. This is present to reflect the realities of physiology. A large step change in heart rate could imply an error in the new heart rate, so the rate at which the heart rate that is shared with the outside world is allowed to approach the calculated heart rate based on the old and new, trends is limited to 4 BPM per second. As an example, if the previous heart rate was 60 and the newly calculated heart rate is 72, the heart rate sent out of the Life Signs Detection System will be 64, then 68 one second later, then 72 a second after that.

The math required to convert the filtered (averaged) inter-beat interval to a beats-per-second heart rate is simple. Since there are 32 clock ticks per second, the heart rate is (32/avg. inter-beat interval)*60. For the example above, this works out to (32/34.5)*60=55 BPM.

Remote Communication

A sensor in the Life Sighs Detection System (LSDS) communicates with a health hub (some kind of PC).

Figure 30:
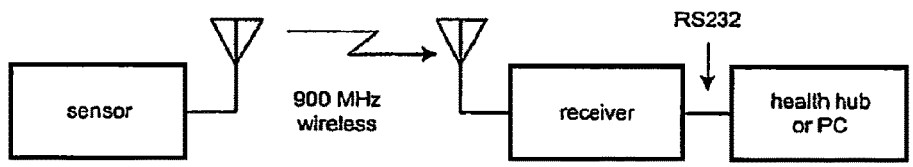
FIG. 30 is an operational overview of the communication to a serial port.

The wireless network connects a single sensor to a health hub via a receiver. The range is preferred to allow for reliable operation at 20 feet. The receiver manages the decoding of the data stream being received from the sensor. The link from the receiver to the health hub is simple serial RS232 at a 9600 baud rate as shown in FIG. 30. The health hub may be any small device having a processor, preferably a PC (desktop or laptop) or a PDA.

Physical Layer

A simple, low cost RF transceiver operating at 900 MHz may be used at both ends of the wireless link. Versions using transceivers would be capable of two-way communication.

Data Link Layer

Figure 31:
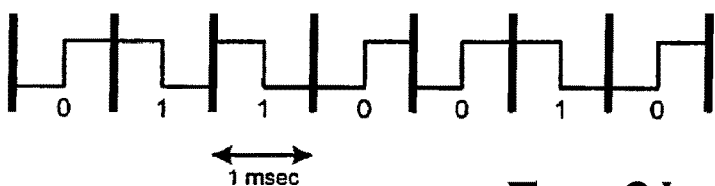
FIG. 31 is an example of a bit stream.
Figure 32:
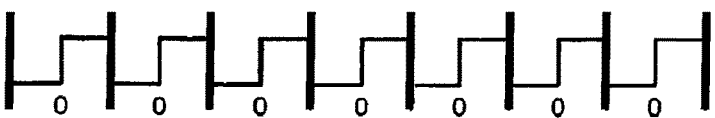
FIG. 32 is an example of a bit stream leader with all zeroes.
Figure 48:
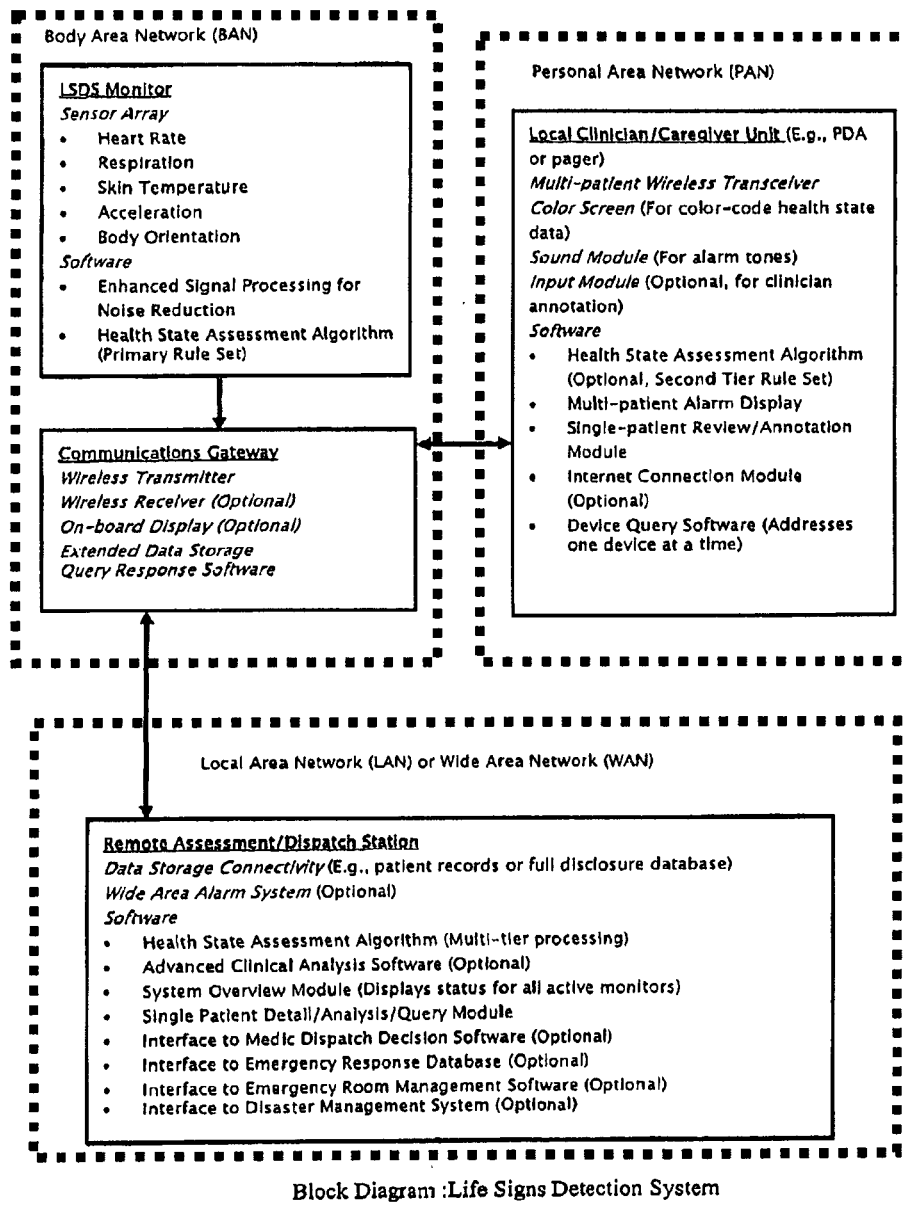
FIG. 48 is a Block Diagram of the Life Signs Detection System

Low cost RF modules tend to have two specific problems. First, as they are susceptible to noise, particularly in the absence of a transmitted signal, receivers tend to have noise pulses at random times. This means that the RF modules are not suited for sending asynchronous data. Second, the RF modules appear unable to hold a "high" level for longer than 10 or 15 milliseconds. This is most likely due to AGC circuitry. The modules therefore seem more content to see constantly changing data. One solution to these two shortcomings is to Manchester encode the data being sent through the RF channel. This not only forces the data to change very often, but it reduces the sensitivity to noise. The bit rate will be 1 msec, and a "0" is encoded as a rising edge (01) in the middle of the bit time, and a "1" is encoded as a falling edge (10). An example bit stream is shown in FIG. 31:

In order for the receiver to recover the timing of the bit stream and hence understand when the start and middle of the bit time is, the transmitter must precede the actual data packet with a series of all 0's. The receiver will recover the bit timing by looking for consistent falling edges. The exact number of 0's in this leader is not important as long as it generates enough clock edges for the receiver to look onto it. Eight to 16 bits should be fine. An all 0's leader corresponds to the encoded data stream shown in FIG. 32:

FIG. 48 is block diagram of the communication system of the present invention. The LSDS system preferably comprises a Body Area Network (BAN), a Personal Area Network (PAN), and a Local Area Network (LAN) or Wide Area Network (WAN). The BAN, in turn, comprises an LDS Monitor having a sensor array and software. The software provides signal processing to reduce signal noise and also provides the health state assessment algorithm together with its primary rule set. Within the BAN is also located a Communications Gateway comprising a wireless transmitter, data storage and query response software together with an optional wireless receiver and an on-board display.

The Communications Gateway enables two way communication with both the PAN and the LAN or WAN. The PAN comprises a Local Clinician/Caregiver Unit, that may be implemented in a PDA or pager. It provides a multi-patient wireless transceiver, color screen (for color-code health state data), sound module (for alarm tones) and an optional input module (for clinician annotation). The PAN further preferably comprises software having a health state assessment algorithm with optional second tier rule sets, a multi-patient alarm display, a single-patient review/annotation module, an optional internet connection module and device query software (for addressing individual devices).

The LAN or WAN comprises a Remote Assessment/Dispatch Station that provides data storage connectivity with typically patient records or a full disclosure database and optionally a wide area alarm system. It further comprises software including a health assessment algorithm, optional clinical analysis software, a system overview module to display the status of all active monitors, a single patient detail/analysis/query module, and several further optional features. Among these optional features are an interface to Medic Dispatch Decision Software, to Emergency Response Databases, to Emergency Room Management Software, and to Disaster Management Systems.

Application Layer

Physiological information is transmitted out of the sensor on a periodic basis. This information is sent in packets in order to provide error detection and noise immunity. The packet format is:

[leader] [header 1] [header 2] [data] [checksum]

The header is a 16-bit pattern that allows the receiver to identify the start of a valid packet. The 10-byte data field is a number of bytes that describe the physiological condition of the wearer of the sensor. Lastly, the checksum is a 16-bit code that helps determine if the data was received without error. Header 1 is 0x0d, while header 2 is 0x1c.

The 10-byte data field is encoded as follows:
- byte 1=sensor ID (valid range is 1 through 250)
- byte 2=health status, where
  - 0=black (no sensor data available)
  - 1=blue (uncertain or unreliable data
  - 2=red (health is very poor)
  - 3=yellow (health is marginal)
  - 4=green (A-OK)
- byte 3=activity level, where
  - 0=no activity
  - 1=low level of activity (e.g. slow rolling, deep knee bends)
  - 2=medium level of activity (e.g. walking)
  - 3=high level of activity (e.g. running)
- byte 4=temperature, signed integer, in degrees C.
- byte 5=heart rate, where
  - 0 through 240=heart rate, in beats per minute
  - 250=strap leads off
  - 251=strap leads on, but cannot determine heart rate due to too many extra pulses (e.g. noise)
  - 252=strap leads on, but cannot determine heart rate due to too many missing pulses (e.g. ECG signal level too low)
- byte 6=battery voltage status, where
  - 0=high
  - 1=moderate
  - 2=low
- byte 7=orientation, where
- upper 4 bitd=up/down axis, where
  - 0000=not stable enough to determine orientation
  - 0001=upright
  - 0010=slanted
  - 0011=horizontal
  - 0100=inverted
- lower 4 bits=side-to-side axis
- byte 8=respiration rate, where
  - 0 through 100=respiration rate, in breaths per minute
  - 250=cannot determine respiration rate (e.g. too much noise)
- byte 9=confidence score of the overall health state assessment
- byte 10=spare byte available for debug, testing, or future use The checksum is a 16-bit summation of each of the data bytes. The summing is done byte-wide, but the result is 16-bits wide.

Figure 33:
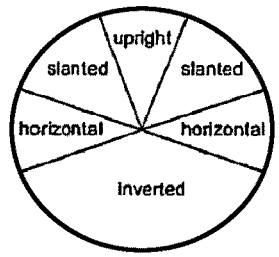
FIG. 33 is a diagram so show how orientation is interpreted.

All multi-byte entities are transmitted little-endian (lowest byte first). The only data that is affected by this rule is the 16-bit checksum since all other protocol elements are bytes. Orientation is interpreted using the diagram of FIG. 33.

What is claimed is:

1. A life signs detection system for monitoring one significant vital sign and one indirect life sign of subjects, said system comprising:
   a plurality of wearable platforms, each wearable platform comprising:
      a heart rate sensor configured to detect a heart rate;
      a body motion sensor configured to detect motion;
      a respiration rate sensor configured to determine respiration rate by detecting motion of a subject;
      a temperature sensor configured to detect a temperature;
      a processor comprising a rule processing engine configured to execute a health state assessment algorithm that performs a medical evaluation and determines a confidence level for the evaluation, said algorithm comprising a rule set to calculate a health state classification and a decision confidence score corresponding to an indicator of confidence; and
      a transmitter configured to transmit local sensor data of medical state information detected by sensors of the wearable platform, the local sensor data of medical state information comprising heart rate, motion, respiration rate, and temperature, and configured to transmit results of the medical evaluation and the decision confidence score;
   a plurality of local hubs each comprising:
      an external display for displaying the results of the medical evaluation;
      a local transceiver hub configured to accept connection from the external display; and
      a receiver configured to receive local sensor data from said wearable platforms; and
   a remote base station configured to receive information from a plurality of local hubs.

2. The life signs detection system of claim 1 wherein the processing engine is configured to perform the medical evaluation and determine the confidence level for the evaluation based on a subject personal baseline dependent rule set and tabulated parameter values.

3. The life signs detection system of claim 2, wherein the rule processing engine is configured to execute rule sets that vary depending upon general characteristics of a subject population.

4. The life signs detection system of claim 1 wherein the respiration rate sensor detects abdominal motion of the subject.

5. The life signs detection system of claim 1 wherein said algorithm comprises tabulated interpretation rules and tabulated boundary conditions and tabulated abnormal values for each personal baseline.

6. The life signs detection system of claim 1 wherein the transmitter of the wearable platform is a short range RF transmitter having low bandwidth output for local sensor data.

7. The life signs detection system of claim 1 wherein the local transceiver hub comprises a short range RF transceiver, a medium or long range transmitter/transceiver and a processor.

8. The life signs detection system of claim 1 wherein said local sensor data comprises periodic and on demand digital data packets of medical state information from said wearable platforms.

9. The life signs detection system of claim 1 wherein said remote base station is a PDA.

10. The life signs detection system of claim 1 wherein said algorithm estimates the likelihood of injury.

11. The life signs detection system of claim 1 wherein said algorithm estimates the likelihood of an injury and the nature of the injury.

12. The life signs detection system of claim 1 wherein the processing engine is configured to perform the medical evaluation and determine the confidence level for the evaluation based on a subject personal baseline dependent rule set.

13. The life signs detection system of claim 1, wherein the processor is configured to assign corresponding colors to the health state classification and the decision confidence score corresponding to the indicator of confidence to provide the health state classification and the decision confidence score with color coding, and wherein said display is configured to display the color coded health state classifications and decision confidence score.

14. The life signs detection system of claim 1, wherein the rule set can be modified by a user based on clinical experience.

15. The life signs detection system of claim 1, wherein the respiration rate sensor comprises a deformation transducer element that varies in electrical resistance as a subject's chest or abdomen expands and contracts due to respiration.

16. The life signs detection system of claim 15, wherein the respiration rate sensor comprises:
- a flexible, variable resistance element; and
- a compliant backing element coupled to the resistance element,
- wherein a resistance of the backing element increases as a radius of curvature of the backing element decreases.

* * * * *